United States Patent
Kim et al.

(10) Patent No.: US 11,872,253 B2
(45) Date of Patent: Jan. 16, 2024

(54) METHOD FOR PRODUCING MARINE ALGAE-DERIVED AGAROTRIOSE, AND USE THEREOF AS PREBIOTIC

(71) Applicant: Korea University Research and Business Foundation, Seoul (KR)

(72) Inventors: Kyoung Heon Kim, Seoul (KR); Yong-Su Jin, Champaign, IL (US); Eun-Ju Yun, Seoul (KR); Dong-Hyun Kim, Busan (KR); Sora Yu, Gyeonggi-do (KR); Kyung-Mun Cho, Gyeonggi-do (KR); Na Jeong Park, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 16 days.

(21) Appl. No.: 17/724,386

(22) Filed: Apr. 19, 2022

(65) Prior Publication Data
US 2022/0241349 A1    Aug. 4, 2022

Related U.S. Application Data

(62) Division of application No. 16/764,742, filed as application No. PCT/KR2018/014003 on Nov. 15, 2018, now Pat. No. 11,337,999.

(30) Foreign Application Priority Data

Nov. 16, 2017   (KR) .................. 10-2017-0153350

(51) Int. Cl.
 *C12P 19/00* (2006.01)
 *A61K 35/44* (2015.01)
 (Continued)

(52) U.S. Cl.
 CPC ............ *A61K 35/44* (2013.01); *A23L 33/125* (2016.08); *A23L 33/135* (2016.08); *A23L 33/40* (2016.08);
 (Continued)

(58) Field of Classification Search
 CPC ...................................... C12P 19/00
 See application file for complete search history.

(56) References Cited

U.S. PATENT DOCUMENTS

2010/0025949 A1    10/2010   Barboza et al.

FOREIGN PATENT DOCUMENTS

| CN | 1593433 A | 3/2005 |
|----|-----------|--------|
| CN | 103468661 A | 12/2013 |

(Continued)

OTHER PUBLICATIONS

Chi et al., "Agar degradation by microorganisms and agar-degrading enzymes," Appl Microbiol Biotechnol 94:917-930, 2012.*

(Continued)

*Primary Examiner* — Rosanne Kosson
(74) *Attorney, Agent, or Firm* — Sughrue Mion, PLLC

(57) ABSTRACT

The present invention relates to a method for producing marine algae-derived agarotriose, and a use thereof as a prebiotic. More specifically, the present invention investigates the characteristics of agarotriose as a prebiotic which is selectively metabolized by probiotic microorganisms, thereby enabling agarotriose to be used as an anti-cancer or anti-inflammatory agent in the fields of food and pharmaceuticals, and enabling agarotriose to be obtained at high yield through efficient purification with minimal loss after enzymatic hydrolysis of a red algae-derived polysaccharide without pre-treatment.

5 Claims, 12 Drawing Sheets

Specification includes a Sequence Listing.

(51) Int. Cl.
  *A23L 33/125*  (2016.01)
  *A23L 33/135*  (2016.01)
  *A23L 33/00*  (2016.01)
  *A61K 35/745*  (2015.01)
  *A61K 47/26*  (2006.01)
  *A61K 35/00*  (2006.01)

(52) U.S. Cl.
  CPC ............ *A61K 35/745* (2013.01); *A61K 47/26* (2013.01); *C12P 19/00* (2013.01); *A23V 2002/00* (2013.01); *A23V 2400/529* (2023.08); *A61K 2035/115* (2013.01)

(56) References Cited

FOREIGN PATENT DOCUMENTS

| | | | |
|---|---|---|---|
| CN | 104780943 | A | 7/2015 |
| JP | 7-322886 | A | 12/1995 |
| KR | 10-2000-0064728 | A | 11/2000 |
| KR | 10-1521711 | B1 | 5/2015 |
| KR | 10-2017-0114379 | A | 10/2017 |

OTHER PUBLICATIONS

International Search Report for PCT/KR2018/014003, dated Feb. 21, 2019.
Marjolaine Martin et al., "Microorganisms living on macroalgae: diversity, interactions, and biotechnological applications", Appl Microbiol Biotechnol, 2014, pp. 2917-2935, vol. 98.

* cited by examiner

1: Agarose substrate
2: Agarose + BpGH16A
3: BpGH16A reaction products + BpGH117
4: Agarose + BpGH16A and BpGH117

A. *Bifidobacterium longum* subsp. *infantis* ATCC 17930

B. *Bifidobacterium longum* subsp. *infantis* ATCC 15702

A. *Bifidobacterium bifidum* DSM 20082

B. *Bifidobacterium kashiwanohense* DSM 21854

FIG. 17

| Agarotriose (DP3) ||
|---|---|
| Purity (%) | Yield (%, w/w) |
| 90.2 | 40.0 |

SEQUENCE LISTING

```
<160> NUMBER OF SEQ ID NOS: 6

<210> SEQ ID NO 1
<211> LENGTH: 316
<212> TYPE: PRT
<213> ORGANISM: Bacteroides plebeius DSM 17135

<400> SEQUENCE: 1

Met Lys Arg Lys Leu Phe Thr Ile Cys Leu Ala Ser Leu Gln Phe Ala
1               5                   10                  15

Cys Ala Ala Glu Asn Leu Asn Asn Lys Ser Tyr Glu Trp Asp Ile Tyr
            20                  25                  30

Pro Val Pro Ala Asn Ala Gly Asp Gly Met Val Trp Lys Leu His Pro
        35                  40                  45

Gln Ser Asp Asp Phe Asn Tyr Ile Ala Asp Glu Lys Asp Lys Gly Lys
    50                  55                  60

Glu Phe Tyr Ala Lys Trp Thr Asp Phe Tyr His Asn His Trp Thr Gly
65                  70                  75                  80

Pro Ala Pro Thr Ile Trp Gln Arg Asp His Val Ser Val Ser Asp Gly
            85                  90                  95

Phe Leu Lys Ile Arg Ala Ser Arg Pro Glu Asp Val Pro Leu Lys Lys
            100                 105                 110

Val Val Ser Gly Pro Asn Thr Lys Glu Leu Pro Gly Thr Tyr Thr Gly
            115                 120                 125

Cys Ile Thr Ser Lys Thr Arg Val Lys Tyr Pro Val Tyr Val Glu Ala
    130                 135                 140

Tyr Ala Lys Leu Ser Asn Ser Thr Met Ala Ser Asp Val Trp Met Leu
145                 150                 155                 160

Ser Pro Asp Asp Thr Gln Glu Ile Asp Ile Ile Glu Ala Tyr Gly Gly
            165                 170                 175

Asp Arg Asp Gly Gly Gly Tyr Gly Ala Asp Arg Leu His Leu Ser His
            180                 185                 190

His Ile Phe Ile Arg Gln Pro Phe Lys Asp Tyr Gln Pro Lys Asp Ser
        195                 200                 205

Gly Ser Trp Tyr Lys Asp Asp Lys Gly Thr Leu Trp Arg Asp Asp Phe
    210                 215                 220
```

-continued

His Arg Val Gly Val Phe Trp Lys Asp Pro Phe Thr Leu Glu Tyr Tyr
225                 230                 235                 240

Val Asp Gly Glu Leu Val Arg Thr Ile Ser Gly Lys Asp Ile Ile Asp
            245                 250                 255

Pro Asn Asn Tyr Thr Gly Gly Thr Gly Leu Val Lys Asp Met Asp Ile
            260                 265                 270

Ile Ile Asn Met Glu Asp Gln Ser Trp Arg Ala Val Lys Gly Leu Ser
        275                 280                 285

Pro Thr Asp Glu Glu Leu Lys Asn Val Glu Asp His Thr Phe Leu Val
    290                 295                 300

Asp Trp Ile Arg Val Tyr Thr Leu Val Pro Glu Glu
305                 310                 315

<210> SEQ ID NO 2
<211> LENGTH: 402
<212> TYPE: PRT
<213> ORGANISM: Bacteroides plebeius DSM 17135

<400> SEQUENCE: 2

Met Arg Lys Ile Ile Phe Ala Ala Gly Met Met Ser Leu Leu Ala Ala
1               5                   10                  15

Cys Gly Asn Thr Gly Asn Thr Gln Thr Ile Ala Val Asp Asp Thr Gln
            20                  25                  30

Asn Tyr Asp Glu Arg Lys Ala Asp Ser Leu Gly Ile Pro Lys Gly Asn
        35                  40                  45

Lys Leu Ser Ala Ala Met Lys Arg Ala Met Lys Trp Glu Asn His Asp
50                  55                  60

Asn Lys Trp Phe Phe Glu Tyr Lys Met Glu Pro Leu Lys Gly Asp Leu
65                  70                  75                  80

Ala Tyr Glu Glu Gly Val Val Arg Asp Pro Ser Ala Met Leu Lys
                85                  90                  95

Ile Gly Asp Thr Tyr Tyr Val Trp Tyr Ser Lys Ser Tyr Gly Pro Thr
            100                 105                 110

Gln Gly Phe Ala Gly Asp Ile Glu Lys Asp Lys Val Phe Pro Trp Asp
        115                 120                 125

Arg Cys Asp Ile Trp Tyr Ala Thr Ser Lys Asp Gly Leu Thr Trp Lys
130                 135                 140

Glu Gln Gly Ile Ala Val Lys Arg Gly Glu Lys Gly Ala Tyr Asp Asp
145                 150                 155                 160

Arg Ser Val Phe Thr Pro Glu Val Met Glu Trp Lys Gly Lys Tyr Tyr
                165                 170                 175

Leu Cys Tyr Gln Ala Val Lys Ser Pro Tyr Thr Val Arg Val Lys Asn
            180                 185                 190

Thr Ile Gly Met Ala Cys Ala Asp Ser Pro Glu Gly Leu Trp Thr Lys
        195                 200                 205

Thr Asp Lys Pro Val Leu Glu Pro Ser Asp Thr Gly Glu Trp Glu Gly
    210                 215                 220

Asp Glu Asp Asn Arg Phe Lys Val Val Ser Lys Gly Asp Phe Asp Ser
225                 230                 235                 240

His Lys Val His Asp Pro Cys Ile Ile Pro Tyr Asn Gly Lys Phe Tyr
                245                 250                 255

Met Tyr Tyr Lys Gly Glu Arg Met Gly Glu Glu Ile Thr Trp Gly Gly
            260                 265                 270

Arg Glu Ile Lys His Gly Val Ala Ile Ala Glu Asn Pro Met Gly Pro
        275                 280                 285

Tyr Val Lys Ser Glu Tyr Asn Pro Ile Ser Asn Ser Gly His Glu Val
            290                 295                 300

Cys Val Trp Pro Tyr Lys Gly Gly Ile Ala Ser Leu Ile Thr Thr Asp
305                 310                 315                 320

Gly Pro Glu Lys Asn Thr Leu Gln Trp Ser Pro Asp Gly Ile Asn Phe
                325                 330                 335

Glu Ile Met Ser Val Val Lys Gly Ala Pro His Ala Ile Gly Leu Asn
                340                 345                 350

Arg Ser Ala Asp Ala Glu Lys Glu Pro Thr Glu Ile Leu Arg Trp Gly
            355                 360                 365

Leu Thr His Ile Tyr Asn Ser Ser Asp Tyr Gln Ser Ile Met Arg Phe
            370                 375                 380

Ser Thr Trp Thr Leu Gln Thr His Thr Ala Lys Gly Glu Ser Lys Glu
385                 390                 395                 400

Arg Lys

<210> SEQ ID NO 3
<211> LENGTH: 691
<212> TYPE: PRT
<213> ORGANISM: Bifidobacterium longum subsp. infantis ATCC 15697

<400> SEQUENCE: 3

Met Glu His Arg Ala Phe Lys Trp Pro Gln Pro Leu Ala Gly Asn Lys
1               5                   10                  15

Pro Arg Ile Trp Tyr Gly Gly Asp Tyr Asn Pro Asp Gln Trp Pro Glu
            20                  25                  30

Glu Val Trp Asp Glu Asp Val Ala Leu Met Gln Gln Ala Gly Val Asn
            35                  40                  45

Leu Val Ser Val Ala Ile Phe Ser Trp Ala Lys Leu Glu Pro Glu Glu
        50                  55                  60

Gly Val Tyr Asp Phe Asp Trp Leu Asp Arg Val Ile Asp Lys Leu Gly
65                  70                  75                  80

Lys Ala Gly Ile Ala Val Asp Leu Ala Ser Gly Thr Ala Ser Pro Pro
                85                  90                  95

Met Trp Met Thr Gln Ala His Pro Glu Ile Leu Trp Val Asp Tyr Arg
            100                 105                 110

Gly Asp Val Cys Gln Pro Gly Ala Arg Gln His Trp Arg Ala Thr Ser
            115                 120                 125

Pro Val Phe Leu Asp Tyr Ala Leu Asn Leu Cys Arg Lys Met Ala Glu
        130                 135                 140

His Tyr Lys Asp Asn Pro Tyr Val Val Ser Trp His Val Ser Asn Glu
145                 150                 155                 160

Tyr Gly Cys His Asn Arg Phe Asp Tyr Ser Glu Asp Ala Glu Arg Ala
                165                 170                 175

Phe Gln Lys Trp Cys Glu Lys Lys Tyr Gly Thr Ile Asp Ala Val Asn
            180                 185                 190

Asp Ala Trp Gly Thr Ala Phe Trp Ala Gln Arg Met Asn Asn Phe Ser
        195                 200                 205

Glu Ile Ile Pro Pro Arg Phe Ile Gly Asp Gly Asn Phe Met Asn Pro
    210                 215                 220

Gly Lys Leu Leu Asp Trp Lys Arg Phe Ser Ser Asp Ala Leu Leu Asp
225                 230                 235                 240

Phe Tyr Lys Ala Glu Arg Asp Ala Leu Leu Glu Ile Ala Pro Lys Pro
                245                 250                 255

```
Gln Thr Thr Asn Phe Met Val Ser Ala Gly Cys Thr Val Leu Asp Tyr
            260                 265                 270

Asp Lys Trp Gly His Asp Val Asp Phe Val Ser Asn Asp His Tyr Phe
            275                 280                 285

Ser Pro Gly Glu Ala His Phe Asp Glu Met Ala Tyr Ala Ala Cys Leu
290                 295                 300

Thr Asp Gly Ile Ala Arg Lys Asn Pro Trp Phe Leu Met Glu His Ser
305                 310                 315                 320

Thr Ser Ala Val Asn Trp Arg Pro Thr Asn Tyr Arg Leu Glu Pro Gly
                325                 330                 335

Glu Leu Val Arg Asp Ser Leu Ala His Leu Ala Met Gly Ala Asp Ala
            340                 345                 350

Ile Cys Tyr Phe Gln Trp Arg Gln Ser Lys Ala Gly Ala Glu Lys Trp
            355                 360                 365

His Ser Ala Met Val Pro His Ala Gly Pro Asp Ser Gln Ile Phe Arg
            370                 375                 380

Asp Val Cys Glu Leu Gly Ala Asp Leu Asn Lys Leu Ala Asp Glu Gly
385                 390                 395                 400

Leu Leu Ser Thr Lys Leu Val Lys Ser Lys Val Ala Ile Val Phe Asp
                405                 410                 415

Tyr Glu Ser Gln Trp Ala Thr Glu His Thr Ala Thr Pro Thr Gln Glu
            420                 425                 430

Val Arg His Trp Thr Glu Pro Leu Asp Trp Phe Arg Ala Leu Ala Asp
            435                 440                 445

Asn Gly Leu Thr Ala Asp Val Val Pro Val Arg Gly Pro Trp Asp Glu
            450                 455                 460

Tyr Glu Ala Val Val Leu Pro Ser Leu Ala Ile Leu Ser Glu Gln Thr
465                 470                 475                 480

Thr Arg Arg Val Arg Glu Tyr Val Ala Asn Gly Gly Lys Leu Phe Val
                485                 490                 495

Thr Tyr Tyr Thr Gly Leu Val Asp Asp Arg Asp His Val Trp Leu Gly
            500                 505                 510

Gly Tyr Pro Gly Ser Ile Arg Asp Val Val Gly Val Arg Val Glu Glu
            515                 520                 525

Phe Ala Pro Met Gly Thr Asp Ala Pro Gly Thr Met Asp His Leu Asp
530                 535                 540

Leu Asp Asn Gly Thr Val Ala His Asp Phe Ala Asp Val Ile Thr Ser
545                 550                 555                 560

Val Ala Asp Thr Ala His Val Val Ala Ser Phe Lys Ala Asp Lys Trp
                565                 570                 575

Thr Gly Phe Asp Gly Ala Pro Ala Ile Thr Val Asn Asp Phe Gly Asp
            580                 585                 590

Gly Lys Ala Ala Tyr Val Gly Ala Arg Leu Gly Arg Glu Gly Leu Ala
            595                 600                 605

Lys Ser Leu Pro Ala Leu Leu Glu Glu Leu Gly Ile Glu Thr Ser Ala
            610                 615                 620

Glu Asp Asp Arg Gly Glu Val Leu Arg Val Glu Arg Ala Asp Glu Thr
625                 630                 635                 640

Gly Glu Asn His Phe Val Phe Leu Phe Asn Arg Thr His Asp Val Ala
                645                 650                 655

Val Val Asp Val Glu Gly Glu Pro Leu Val Ala Ser Leu Ala Gln Val
            660                 665                 670
```

-continued

```
Asn Glu Ser Glu His Thr Ala Ala Ile Gln Pro Asn Gly Val Leu Val
            675                 680                 685

Val Lys Leu
    690

<210> SEQ ID NO 4
<211> LENGTH: 1023
<212> TYPE: PRT
<213> ORGANISM: Bifidobacterium longum subsp. infantis ATCC 15697

<400> SEQUENCE: 4

Met Thr Asp Val Thr His Val Asp Arg Ala Ser Gln Ala Trp Leu Thr
1               5                   10                  15

Asp Pro Thr Val Phe Glu Val Asn Arg Thr Pro Ala His Ser Ser His
            20                  25                  30

Lys Trp Tyr Ala Arg Asp Pro Gln Ser Gly Gln Trp Ser Asp Leu Lys
        35                  40                  45

Gln Ser Leu Asp Gly Glu Trp Arg Val Glu Val Gln Ala Ala Asp
    50                  55                  60

Ile Asn Leu Glu Glu Glu Pro Ala Thr Ala Glu Ser Phe Asp Asp Ser
65                  70                  75                  80

Ser Phe Glu Arg Ile Gln Val Pro Gly His Leu Gln Thr Ala Gly Leu
                85                  90                  95

Met Asn His Lys Tyr Val Asn Val Gln Tyr Pro Trp Asp Gly His Glu
            100                 105                 110

Asn Pro Leu Glu Pro Asn Ile Pro Glu Asn Asn His Val Ala Leu Tyr
        115                 120                 125

Arg Arg Lys Phe Thr Val Ser Ala Pro Val Ala Asn Ala Lys Gln Ala
    130                 135                 140

Gly Gly Ser Val Ser Ile Val Phe His Gly Met Ala Thr Ala Ile Tyr
145                 150                 155                 160

Val Trp Val Asn Gly Ala Phe Val Gly Tyr Gly Glu Asp Gly Phe Thr
                165                 170                 175

Pro Asn Glu Phe Asp Ile Thr Gly Leu Leu His Asp Gly Glu Asn Val
            180                 185                 190

Val Ala Val Ala Cys Tyr Glu Tyr Ser Ser Ala Ser Trp Leu Glu Asp
        195                 200                 205

Gln Asp Phe Trp Arg Leu His Gly Leu Phe Arg Ser Val Glu Leu Ala
    210                 215                 220

Ala Arg Pro His Val His Ile Glu Asn Thr Gln Ile Glu Ala Asp Trp
225                 230                 235                 240

Asp Pro Glu Ala Gly Thr Ala Ser Leu Asp Ala Ala Leu Thr Val Leu
                245                 250                 255

Asn Ala Thr Asp Ala Ala Thr Val Arg Ala Thr Leu Lys Asp Ala Asp
            260                 265                 270

Gly Asn Thr Val Trp Gln Thr Gly Asp Ala Glu Ala Gln Thr Ala
        275                 280                 285

Leu Ser Ser Gly Pro Leu Gln Gly Ile Glu Pro Trp Ser Ala Glu Ser
    290                 295                 300

Pro Thr Leu Tyr Glu Leu Asp Val Asp Val Ile Asp Gln Ala Gly Asp
305                 310                 315                 320

Val Ile Glu Cys Thr Ser Gln Lys Val Gly Phe Arg Arg Phe Arg Ile
                325                 330                 335

Glu Asp Gly Ile Leu Thr Ile Asn Gly Lys Arg Ile Val Phe Lys Gly
            340                 345                 350
```

```
Ala Asp Arg His Glu Phe Asp Ala Glu Arg Gly Arg Ala Ile Thr Glu
            355                 360                 365

Gln Asp Met Ile Asp Asp Val Val Phe Cys Lys Arg His Asn Ile Asn
370                 375                 380

Ser Ile Arg Thr Ser His Tyr Pro Asn Gln Glu Arg Trp Tyr Glu Leu
385                 390                 395                 400

Cys Asp Glu Tyr Gly Ile Tyr Leu Ile Asp Glu Thr Asn Leu Glu Ala
                405                 410                 415

His Gly Ser Trp Ser Leu Pro Gly Asp Val Leu Thr Glu Asp Thr Ile
            420                 425                 430

Val Pro Gly Ser Lys Arg Glu Trp Glu Gly Ala Cys Val Asp Arg Val
            435                 440                 445

Asn Ser Met Met Arg Arg Asp Tyr Asn His Pro Ser Val Leu Ile Trp
450                 455                 460

Ser Leu Gly Asn Glu Ser Tyr Val Gly Asp Val Phe Arg Ala Met Tyr
465                 470                 475                 480

Lys His Val His Asp Ile Asp Pro Asn Arg Pro Val His Tyr Glu Gly
                485                 490                 495

Val Thr His Asn Arg Asp Tyr Asp Asp Val Thr Asp Ile Glu Thr Arg
            500                 505                 510

Met Tyr Ser His Ala Asp Glu Ile Glu Lys Tyr Leu Lys Asp Pro
            515                 520                 525

Lys Lys Pro Tyr Leu Ser Cys Glu Tyr Met His Ala Met Gly Asn Ser
            530                 535                 540

Val Gly Asn Met Asp Glu Tyr Thr Ala Leu Glu Arg Tyr Pro Lys Tyr
545                 550                 555                 560

Gln Gly Gly Phe Ile Trp Asp Phe Ile Asp Gln Ala Ile Tyr Ala Thr
                565                 570                 575

Gln Pro Asp Gly Thr Arg Ser Leu Arg Tyr Gly Gly Asp Phe Gly Asp
            580                 585                 590

Arg Pro Ser Asp Tyr Glu Phe Ser Gly Asp Gly Leu Leu Phe Ala Asp
            595                 600                 605

Arg Lys Pro Ser Pro Lys Ala Gln Glu Val Lys Gln Leu Tyr Ser Asn
            610                 615                 620

Val His Ile Asp Val Thr Lys Asp Ser Val Ser Val Lys Asn Asp Asn
625                 630                 635                 640

Leu Phe Thr Ala Thr Gly Asp Tyr Val Phe Val Leu Ser Val Leu Ala
                645                 650                 655

Asp Gly Lys Pro Val Trp Gln Ser Thr Arg Arg Phe Asp Val Pro Ala
            660                 665                 670

Gly Glu Thr Arg Thr Phe Asp Val Ala Trp Pro Val Ala Ala Tyr Arg
            675                 680                 685

Ala Asp Ala Arg Glu Leu Val Leu Gln Val Ser Gln Arg Leu Ala Lys
690                 695                 700

Ala Thr Asp Trp Ala Glu Ser Gly Tyr Glu Leu Ala Phe Gly Gln Ala
705                 710                 715                 720

Val Val Pro Ala Asp Ala Thr Ala Thr Pro Asp Thr Lys Pro Ala Asp
                725                 730                 735

Gly Thr Ile Thr Val Gly Arg Trp Asn Ala Gly Val Arg Gly Ala Gly
            740                 745                 750

Arg Glu Val Leu Leu Ser Arg Thr Gln Gly Gly Met Val Ser Tyr Thr
            755                 760                 765
```

Phe Ala Gly Asn Glu Phe Val Leu Arg Arg Pro Ala Ile Thr Thr Phe
770                 775                 780

Arg Pro Leu Thr Asp Asn Asp Arg Gly Ala Gly His Gly Phe Glu Arg
785                 790                 795                 800

Val Gln Trp Leu Gly Ala Gly Arg Tyr Ala Arg Cys Val Asp Asn Val
                805                 810                 815

Leu Glu Gln Ile Asp Asp Ser Thr Leu Lys Gly Thr Tyr Thr Tyr Glu
            820                 825                 830

Leu Ala Thr Ala Gln Arg Thr Lys Val Thr Val Ser Tyr Thr Ala His
        835                 840                 845

Thr Asp Gly Arg Val Asn Leu His Val Glu Tyr Pro Gly Glu Gln Gly
850                 855                 860

Asp Leu Pro Thr Ile Pro Ala Phe Gly Ile Glu Trp Thr Leu Pro Val
865                 870                 875                 880

Gln Tyr Thr Asn Leu Arg Phe Phe Gly Thr Gly Pro Glu Glu Thr Tyr
                885                 890                 895

Leu Asp Arg Lys His Ala Lys Leu Gly Val Trp Asn Thr Asn Ala Phe
            900                 905                 910

Ala Asp His Ala Pro Tyr Leu Met Pro Gln Glu Thr Gly Asn His Glu
        915                 920                 925

Asp Val Arg Trp Ala Glu Ile Thr Asp Asp His Gly His Gly Met Arg
930                 935                 940

Val Ser Arg Ala Asp Gly Ala Ala Pro Phe Ala Val Ser Leu Leu Pro
945                 950                 955                 960

Tyr Ser Ser Phe Met Leu Glu Glu Ala Gln His Gln Asp Glu Leu Pro
                965                 970                 975

Lys Pro Lys His Met Phe Leu Arg Val Leu Ala Ala Gln Met Gly Val
            980                 985                 990

Gly Gly Asp Asp Ser Trp Met Ser Pro Val His Pro Gln Tyr His Ile
        995                 1000                1005

Pro Ala Asp Lys Pro Ile Ser Leu Asp Val Asp Leu Glu Leu Ile
    1010                1015                1020

<210> SEQ ID NO 5
<211> LENGTH: 598
<212> TYPE: PRT
<213> ORGANISM: Saccharophagus degradans 2-40

<400> SEQUENCE: 5

Met Lys Thr Thr Lys Cys Ala Leu Ala Ala Leu Phe Phe Ser Thr Pro
1               5                   10                  15

Leu Met Ala Ala Asp Trp Asp Gly Ile Pro Val Pro Ala Asp Pro Gly
            20                  25                  30

Asn Gly Asn Thr Trp Glu Leu Gln Ser Leu Ser Asp Asp Phe Asn Tyr
        35                  40                  45

Ala Ala Pro Ala Asn Gly Lys Ser Thr Phe Tyr Ser Arg Trp Ser
    50                  55                  60

Glu Gly Phe Ile Asn Ala Trp Leu Gly Pro Gly Gln Thr Glu Phe Tyr
65                  70                  75                  80

Gly Pro Asn Ala Ser Val Glu Gly Gly His Leu Ile Ile Lys Ala Thr
                85                  90                  95

Arg Lys Pro Gly Thr Thr Gln Ile Tyr Thr Gly Ala Ile His Ser Asn
            100                 105                 110

Glu Ser Phe Thr Tyr Pro Leu Tyr Leu Glu Ala Arg Thr Lys Ile Thr
        115                 120                 125

```
Asn Leu Thr Leu Ala Asn Ala Phe Trp Leu Leu Ser Ser Asp Ser Thr
            130                 135                 140

Glu Glu Ile Asp Val Leu Glu Ser Tyr Gly Ser Asp Arg Ala Thr Glu
145                 150                 155                 160

Thr Trp Phe Asp Glu Arg Leu His Leu Ser His His Val Phe Ile Arg
                    165                 170                 175

Gln Pro Phe Gln Asp Tyr Gln Pro Lys Asp Ala Gly Ser Trp Tyr Pro
                180                 185                 190

Asn Pro Asp Gly Gly Thr Trp Arg Asp Gln Phe Phe Arg Ile Gly Val
                195                 200                 205

Tyr Trp Ile Asp Pro Trp Thr Leu Glu Tyr Tyr Val Asn Gly Glu Leu
            210                 215                 220

Val Arg Thr Val Ser Gly Pro Glu Met Ile Asp Pro Tyr Gly Tyr Thr
225                 230                 235                 240

Asn Gly Thr Gly Leu Ser Lys Pro Met Gln Val Ile Phe Asp Ala Glu
                    245                 250                 255

His Gln Pro Trp Arg Asp Glu Gln Gly Thr Ala Pro Pro Thr Asp Ala
                260                 265                 270

Glu Leu Ala Asp Ser Ser Arg Asn Gln Phe Leu Ile Asp Trp Val Arg
                275                 280                 285

Phe Tyr Lys Pro Val Ala Ser Asn Asn Gly Gly Asp Pro Gly Asn
290                 295                 300

Gly Gly Thr Pro Gly Asn Gly Gly Ser Gly Asp Thr Val Val Val Glu
305                 310                 315                 320

Met Ala Asn Phe Ser Ala Thr Gly Lys Glu Gly Ser Ala Val Ala Gly
                    325                 330                 335

Asp Thr Phe Thr Gly Phe Asn Pro Ser Gly Ala Asn Asn Ile Asn Tyr
                340                 345                 350

Asn Thr Leu Gly Asp Trp Ala Asp Tyr Thr Val Asn Phe Pro Ala Ala
                355                 360                 365

Gly Asn Tyr Thr Val Asn Leu Ile Ala Ala Ser Pro Val Thr Ser Gly
            370                 375                 380

Leu Gly Ala Asp Ile Leu Val Asp Ser Ser Tyr Ala Gly Thr Ile Pro
385                 390                 395                 400

Val Ser Ser Thr Gly Ala Trp Glu Ile Tyr Asn Thr Phe Ser Leu Pro
                    405                 410                 415

Ser Ser Ile Tyr Ile Ala Ser Ala Gly Asn His Thr Ile Arg Val Gln
                420                 425                 430

Ser Ser Gly Gly Ser Ala Trp Gln Trp Asn Gly Asp Glu Leu Arg Phe
            435                 440                 445

Thr Gln Thr Asp Ala Asp Thr Gly Thr Asn Pro Pro Ser Thr Ala Ser
    450                 455                 460

Ile Ala Val Glu Ala Glu Asn Phe Asn Ala Val Gly Gly Thr Phe Ser
465                 470                 475                 480

Asp Gly Gln Ala Gln Pro Val Ser Val Tyr Thr Val Asn Gly Asn Thr
                    485                 490                 495

Ala Ile Asn Tyr Val Asn Gln Gly Asp Tyr Ala Asp Tyr Thr Ile Ala
                500                 505                 510

Val Ala Gln Ala Gly Asn Tyr Thr Ile Ser Tyr Gln Ala Gly Ser Gly
            515                 520                 525

Val Thr Gly Gly Ser Ile Glu Phe Leu Val Asn Glu Asn Gly Ser Trp
    530                 535                 540
```

```
Ala Ser Lys Thr Val Thr Ala Val Pro Asn Gln Gly Trp Asp Asn Phe
545                 550                 555                 560

Gln Pro Leu Asn Gly Gly Ser Val Tyr Leu Ser Ala Gly Thr His Gln
                565                 570                 575

Val Arg Leu His Gly Ala Gly Ser Asn Asn Trp Gln Trp Asn Leu Asp
            580                 585                 590

Lys Phe Thr Leu Ser Asn
            595

<210> SEQ ID NO 6
<211> LENGTH: 368
<212> TYPE: PRT
<213> ORGANISM: Saccharophagus degradans 2-40

<400> SEQUENCE: 6

Met Ser Asp Ser Lys Val Asn Lys Lys Leu Ser Lys Ala Ser Leu Arg
1               5                   10                  15

Ala Ile Glu Arg Gly Tyr Asp Glu Lys Gly Pro Glu Trp Leu Phe Glu
            20                  25                  30

Phe Asp Ile Thr Pro Leu Lys Gly Asp Leu Ala Tyr Glu Glu Gly Val
        35                  40                  45

Ile Arg Arg Asp Pro Ser Ala Val Leu Lys Val Asp Asp Glu Tyr His
    50                  55                  60

Val Trp Tyr Thr Lys Gly Glu Gly Glu Thr Val Gly Phe Gly Ser Asp
65                  70                  75                  80

Asn Pro Glu Asp Lys Val Phe Pro Trp Asp Lys Thr Glu Val Trp His
                85                  90                  95

Ala Thr Ser Lys Asp Lys Ile Thr Trp Lys Glu Ile Gly Pro Ala Ile
            100                 105                 110

Gln Arg Gly Ala Ala Gly Ala Tyr Asp Asp Arg Ala Val Phe Thr Pro
        115                 120                 125

Glu Val Leu Arg His Asn Gly Thr Tyr Tyr Leu Val Tyr Gln Thr Val
    130                 135                 140

Lys Ala Pro Tyr Leu Asn Arg Ser Leu Glu His Ile Ala Ile Ala Tyr
145                 150                 155                 160

Ser Asp Ser Pro Phe Gly Pro Trp Thr Lys Ser Asp Ala Pro Ile Leu
                165                 170                 175

Ser Pro Glu Asn Asp Gly Val Trp Asp Thr Asp Glu Asp Asn Arg Phe
            180                 185                 190

Leu Val Lys Glu Lys Gly Ser Phe Asp Ser His Lys Val His Asp Pro
        195                 200                 205

Cys Leu Met Phe Phe Asn Asn Arg Phe Tyr Leu Tyr Tyr Lys Gly Glu
    210                 215                 220

Thr Met Gly Glu Ser Met Asn Met Gly Gly Arg Glu Ile Lys His Gly
225                 230                 235                 240

Val Ala Ile Ala Asp Ser Pro Leu Gly Pro Tyr Thr Lys Ser Glu Tyr
                245                 250                 255

Asn Pro Ile Thr Asn Ser Gly His Glu Val Ala Val Trp Pro Tyr Lys
            260                 265                 270

Gly Gly Met Ala Thr Met Leu Thr Thr Asp Gly Pro Glu Lys Asn Thr
        275                 280                 285

Cys Gln Trp Ala Glu Asp Gly Ile Asn Phe Asp Ile Met Ser His Ile
    290                 295                 300

Lys Gly Ala Pro Glu Ala Val Gly Phe Phe Arg Pro Glu Ser Asp Ser
305                 310                 315                 320
```

```
Asp Asp Pro Ile Ser Gly Ile Glu Trp Gly Leu Ser His Lys Tyr Asp
            325                 330                 335

Ala Ser Trp Asn Trp Asn Tyr Leu Cys Phe Phe Lys Thr Arg Arg Gln
            340                 345                 350

Val Leu Asp Ala Gly Ser Tyr Gln Gln Thr Gly Asp Ser Gly Ala Val
            355                 360                 365
```

METHOD FOR PRODUCING MARINE ALGAE-DERIVED AGAROTRIOSE, AND USE THEREOF AS PREBIOTIC

CROSS-REFERENCE TO RELATED APPLICATIONS

This application is a Divisional application of U.S. application Ser. No. 16/764,742 filed May 15, 2020, which is a National Stage of International Application No. PCT/KR2018/014003 filed Nov. 15, 2018, which claims priority from Korean Patent Application No. 10-2017-0153350 filed Nov. 16, 2017, the disclosures of which are incorporated herein by reference in their respective entireties.

BACKGROUND

1. Field of the Invention

The present invention relates to a method for producing marine algae-derived agarotriose, and a use thereof as a prebiotic.

2. Discussion of Related Art

Prebiotics refer to materials that are selectively fermented by intestinal beneficial bacteria to improve intestinal flora and are beneficial for human health. While studies on the correlation between human diseases and intestinal flora have been recently reported, intestinal flora has been recognized as a second human genome, so that studies in this field have been rapidly developed. In particular, as there are study results reporting that as the distribution of intestinal beneficial flora is increased, obesity, diabetes, and immune functions are improved, research on intestinal flora has been getting more attention.

The prebiotic effect of hydrolysis products of agarose which is a main polysaccharide constituting red algae has been predicted through animal experiments. As a result of orally administering an agarooligosaccharide mixture to rats with obesity induced by a high fat diet, it was confirmed that the degree of distribution of *Bifidobacteria* which is an intestinal beneficial bacteria was increased. In addition, the agarooligosaccharide mixture promoted synthesis of intestinal low-molecular weight fatty acids and induced expression of immune and anti-inflammatory function-related genes. Further, it was confirmed that in the case of a neoagarooligosaccharide mixture produced from agarose by two types of endo-type β-agarase enzymatic reactions, *Bifidobacteria* and *Lactobacillus* were growing under carbon source condition of a neoagarooligosaccharide mixture. However, in this experiment, since a growth test of *Bifidobacteria* and *Lactobacillus* was not performed under a condition in the absence of a neoagarooligosaccharide mixture as a control, there is a problem in that it cannot be exactly known whether the growth is caused by other carbon sources in the medium or by the metabolism of the neoagarooligosaccharide. Further, it was confirmed that when the neoagarooligosaccharide mixture was administered to a rat model, the degree of distribution of *Bifidobacteria* and *Lactobacillus* was increased.

As previously described, since the prebiotics functionality studies of red algae-derived oligosaccharides have used a mixture rather than a purified standard material to date, it is not known at all what effective index components impart a change in the intestinal flora while actually having prebiotic activity. In addition, it is not known how agarose-derived oligosaccharides are metabolized by intestinal effective probiotic microorganisms.

Meanwhile, the main polysaccharide constituting red algae is agarose, and agarose is a polymer in which 3,6-anhydro-L-galactose (hereinafter, referred to as 'AHG') and D-galactose (hereinafter, referred to as 'D-Gal') are alternately linked together through alpha-1,3-bonds and β-1,4-bonds. A previous study established a process for the production of AHG with anti-caries, anti-inflammatory, whitening, and moisturizing functions. Agarooligosaccharides were obtained by pre-treatment of a substrate such as an agarose or agar substrate using a weak acid, acetic acid or a low-concentration neutral buffer, Tris-HC1 buffer (pH 7.4), and neoagarobiose was produced from the agarooligosaccharides through an exo-type β-agarase II enzymatic reaction. In this case, there is a disadvantage in that agarotriose is also produced as a byproduct, and in order to degrade agarotriose into a monosaccharide AHG and galactose, there is a need for introducing an additional enzyme called agarolytic β-galactosidase (ABG). However, agarotriose in the form of Gal-AHG-Gal, which is an oligosaccharide that was considered as a byproduct for the production of AHG in previous studies is currently known to promote beneficial bacteria in the intestinal function of the body and have prebiotic effects by itself through various documents, but a detailed process technology for obtaining purified and pure agarotriose is not known domestically.

SUMMARY OF THE INVENTION

An object of the present invention is to provide a use of agarotriose as a medicine or food material by investigating the metabolism of agarotriose by intestinal effective probiotic microorganisms.

Another object of the present invention is to provide a method for preparing agarotriose by enzymatic hydrolysis and purification.

To achieve the objects, the present invention provides a medicine composition including: one or more substrates selected from the group consisting of agar, agarose, neoagarohexaose, and agarotriose; a *Bacteroides plebeius* strain; and a *Bifidobacterium* strain.

The present invention also provides a method for treating cancer or an inflammatory disease, the method including: administering a therapeutically effective amount of the medicine composition to a subject.

The present invention also provides a food composition including: one or more substrates selected from the group consisting of agar, agarose, neoagarohexaose, and agarotriose; a *Bacteroides plebeius* strain; and a *Bifidobacterium* strain.

The present invention also provides a method for preparing agarotriose, the method including:
  reacting a reaction product with a neoagarobiose hydrolase of SEQ ID NO: 2 or 6, wherein the reaction product is obtained by reacting any one substrate of agar, agarose or neoagaroheaose with a β-agarase of SEQ ID NO: 1 or 5; and
  purifying agarotriose from the resulting product through a size-exclusion column.

The present invention has an effect that the present invention can be used as an anti-cancer or anti-inflammatory material in the fields of medicine and food by investigating the characteristics of agarotriose as a prebiotic which is selectively metabolized by probiotic microorganisms such as *Bacteroides* and *Bifidobacterium*.

Further, the present invention has an effect of enabling agarotriose to be obtained at high yield through efficient purification with minimal loss after enzymatic hydrolysis of a red algae-derived polysaccharide without pre-treatment.

BRIEF DESCRIPTION OF THE DRAWINGS

FIG. 17 illustrates the results of measuring the yield and purity of agarotriose using an HPLC KS-802 sugar column.

DETAILED DESCRIPTION OF EXEMPLARY EMBODIMENTS

Figure 1:
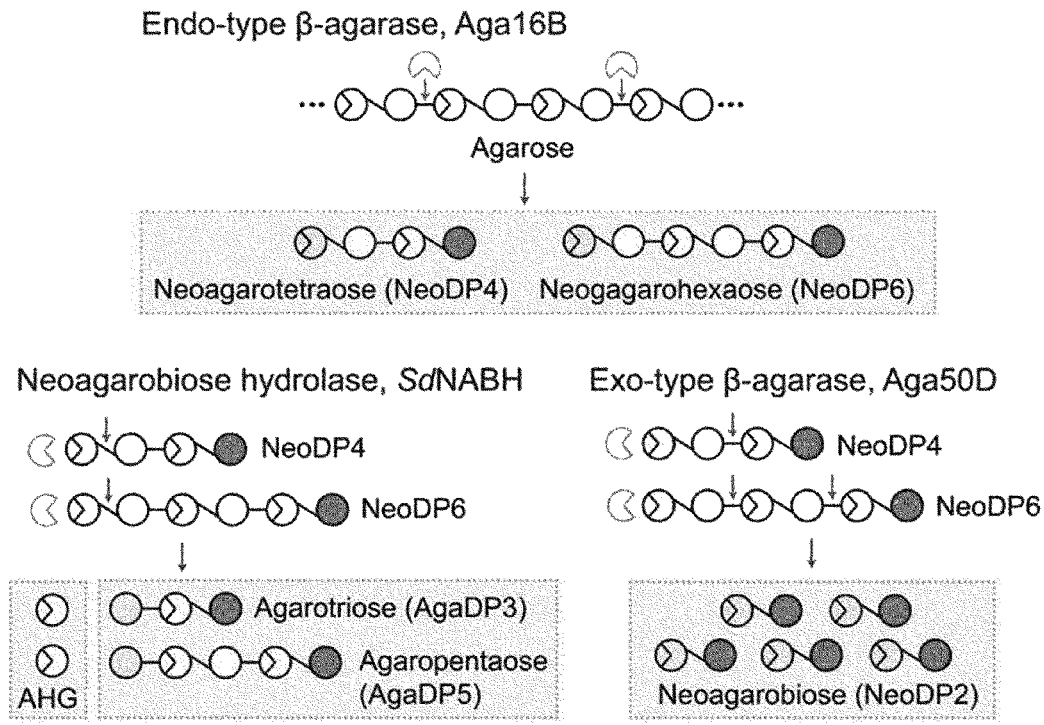
FIG. 1 illustrates a schematic view for producing oligosaccharides with various degrees of polymerization, neoagarobiose, and AHG from agarose through an enzymatic reaction.

The present inventors proved the prebiotic effect of agarotriose by producing agarotriose from agarose which is a main carbohydrate constituting red algae through endo type β-agarase and neoagarobiose hydrolase reactions, purely isolating and purifying only agarotriose among enzymatic reaction products using a size-exclusion chromatography technique, and testing the fermentation ability of agarotriose by probiotic *Bifidobacteria*. Further, since neoagarobiose produced by fermentation of agarotriose by *Bifidobacteria* may be degraded into galactose and AHG by a neoagarobiose hydrolase from *Bacteroides plebeius* which is an intestinal microorganism and the AHG is a bioactive material having prevention of coloncancer and anti-inflammatory effects, it was confirmed that agarotriose could be expected to have not only prebiotic activity but also biological activities such as anti-cancer and anti-inflammation through metabolism by intestinal microorganisms.

Therefore, the present invention provides a medicine composition including: one or more substrates selected from the group consisting of agar, agarose, neoagarohexaose, and agarotriose; a *Bacteroides plebeius* strain; and a *Bifidobacterium* strain.

The *Bacteroides plebeius* strain may include a *Bacteroides plebeius* DSM 17135 strain.

The *Bifidobacterium* strain may include *Bifidobacterium longum* subsp. *infantis* ATCC 17930, *Bifidobacterium longum* subsp. *infantis* ATCC 15702, *B. bifidum* DSM 20082, *B. kashiwanohense* DSM 21854, or the like.

The medicine composition of the present invention is characterized in that a substrate is finally degraded into AHG by a *Bacteroides plebeius* strain and a *Bifidobacterium* strain.

More specifically, AHG may be degraded from a substrate by α β-agarase of SEQ ID NO: 1 and a neoagarobiose hydrolase of SEQ ID NO: 2 derived from *Bacteroides plebeius* DSM 17135 strain, respectively and a β-galactosidase of SEQ ID NO: 3 or 4 derived from *Bifidobacterium longum* subsp. *infantis* ATCC 15697 strain.

The β-agarase is an enzyme which is derived from *Bacteroides plebeius* DSM 17135 and uses agar, agarose, or neoagarohexaose as a substrate to degrade the substrate into neoagarotetraose and neoagarobiose, and may be represented by the amino acid sequences of SEQ ID NO: 1.

The β-agarase may be transcribed and translated through not only a region before and after a coding region of the enzyme, but also a DNA segment associated with production of a polypeptide including an intervening sequence between individual coding segments, that is, a coding gene. Further, a protein having a hydrolytic activity of the agar, agarose, or neoagarohexaose as a variant protein with one or more of substitution, deletion, transposition, addition, and the like of the enzyme is also included in the scope of the enzyme of the present invention, and preferably, includes an amino acid sequence having a sequence identity of 80% or more, 85% or more, 90% or more, 93% or more, 94% or more, 95% or more, 96% or more, 97% or more, 98% or more, and 99% or more with the amino acid sequences set forth in SEQ ID NO: 1.

The β-agarase may be isolated and purified from a supernatant of a *Bacteroides plebeius* DSM 17135 cultures, and may be produced and isolated from strains other than *Bacteroides plebeius* DSM 17135 using a genetic engineering recombinant technology, an artificial chemical synthesis method, or the like. When the genetic engineering recombinant technology is used, it may be replaced by a supernatant or supernate fluid of a culture product of a transformed *E. coli*, but the technology is not particularly limited thereto. According to a specific exemplary embodiment, the β-agarase may be obtained from *E. coli* transformed with a recombinant vector including a nucleic acid sequence of a gene encoding the β-agarase, or cultures thereof.

The neoagarobiose hydrolase is an enzyme that is derived from *Bacteroides plebeius* DSM 17135 and uses neoagarotetraose or neoagarobiose as a substrate to degrade the substrate into agarotriose, galactose, or 3,6-anhydro-L-galactose, and may be represented by the amino acid sequences of SEQ ID NO: 2.

The neoagarobiose hydrolase may be transcribed and translated through not only a region before and after a coding region of the neoagarobiose hydrolase, but also a DNA segment associated with production of a polypeptide including an intervening sequence between individual coding segments, that is, a coding gene. Further, a protein having a hydrolytic activity of the agar, agarose, or neoagarohexaose as a variant protein with one or more of substitution, deletion, transposition, addition, and the like of the enzyme is also included in the scope of the enzyme of the present invention, and preferably, includes an amino acid sequence having a sequence identity of 80% or more, 85% or more, 90% or more, 93% or more, 94% or more, 95% or more, 96% or more, 97% or more, 98% or more, and 99% or more with the amino acid sequences disclosed in SEQ ID NO: 2.

The neoagarobiose hydrolase may be isolated and purified from a supernatant of a *Bacteroides plebeius* DSM 17135 cultures, and may be produced and isolated from strains other than *Bacteroides plebeius* DSM 17135 using a genetic engineering recombinant technology, an artificial chemical synthesis method, or the like. When the genetic engineering recombinant technology is used, it may be replaced by a supernatant or supernate fluid of a culture product of a transformed *E. coli*, but the technology is not particularly limited thereto. According to a specific exemplary embodiment, the neoagarobiose hydrolase may be obtained from *E. coli* transformed with a recombinant vector including a nucleic acid sequence of a gene encoding the neoagarobiose hydrolase, or cultures thereof The β-galactosidase is an enzyme which is derived from *Bifidobacterium longum* subsp. *infantis* ATCC 15697 and degrades agarotriose into neoagarobiose and galactose, is a protein produced from a Blon_2016, Blon_2334 gene, and may be represented by the amino acid sequences of SEQ ID NO: 3 or 4.

The β-galactosidase may be transcribed and translated through not only a region before and after a coding region of the enzyme, but also a DNA segment associated with production of a polypeptide including an intervening sequence between individual coding segments, that is, a coding gene. Further, a protein having a hydrolytic activity of the agarotriose as a variant protein with one or more of substitution, deletion, transposition, addition, and the like of the enzyme is also included in the scope of the enzyme of the present invention, and preferably, includes an amino acid sequence having a sequence identity of 80% or more, 85% or more, 90% or more, 93% or more, 94% or more, 95% or more, 96% or more, 97% or more, 98% or more, and 99% or more with the amino acid sequences disclosed in SEQ ID NO: 3 or 4.

The β-galactosidase may be isolated and purified from a supernatant of a *Bifidobacterium longum* subsp. *infantis* ATCC 15697 cultures, and may be produced and isolated from strains other than *Bifidobacterium longum* subsp. *infantis* ATCC 15697 using a genetic engineering recombinant technology, an artificial chemical synthesis method, or the like. When the genetic engineering recombinant technology is used, it may be replaced by a supernatant or supernate fluid of a culture product of a transformed *E. coli*, but the technology is not particularly limited thereto. According to a specific exemplary embodiment, the β-agarase may be obtained from *E. coli* transformed with a recombinant vector including a nucleic acid sequence of a gene encoding the β-agarase, or cultures thereof In the present specification, "protein" and "polypeptide" are used interchangeably.

In the present invention, the fact that a polypeptide has a specific proportion of sequence identity (for example, 80%, 85%, 90%, 95%, or 99%) with another sequence means that when the two sequences are aligned, the amino acid residues are the same as each other at the proportion at the time of comparing the sequences. The alignment and percent homology or identity may be determined by using those described in any suitable software program publicly known in the art, for example, a document [CURRENT PROTOCOLS IN MOLECULAR BIOLOGY (F. M. Ausubel et al., (eds) 1987 Supplement 30 section 7.7.18)]. Examples of a preferred program include a GCG Pileup program, FASTA (Pearson et al., 1988 Proc. Natl Acad. Sci USA 85:2444-2448), and BLAST (BLAST Manual, Altschul et al., Natl. Cent. Biotechnol. Inf., Natl Lib. Med. (NCIB NLM NIH), Bethesda, MD, and Altschul et al., 1997 NAR25:33893402). Another preferred alignment program is ALIGN Plus (Scientific and Educational Software, PA), and preferably, is an alignment program which uses base parameters. Another available sequence software program is a TFASTA Data Searching Program available in the Sequence Software Package Version 6.0 (Genetics Computer Group, University of Wisconsin, Madison, WI).

As used herein, the term "recombinant" when used in connection with a cell, a nucleic acid, a protein, or a vector indicates that the cell, the nucleic acid, the protein, or the vector is modified by introducing a heterologous nucleic acid or protein or changing an original nucleic acid or protein, or that the cell is derived from a cell thus modified. That is, for example, a recombinant cell expresses a gene which is not found within the original (non-recombinant) form of the cell, or alternatively, the recombinant cell expresses an original gene which is abnormally expressed or not expressed at all upon expression.

In the present specification, "nucleic acid" encompasses single stranded or double stranded DNA and RNA, and a chemical variant thereof "Nucleic acid" and "polynucleotide" may be used interchangeably in the present application. Since the genetic code is degenerate, one or more codons may be used in order to encode a specific amino acid, and the present invention encompasses a polynucleotide encoding a specific amino acid sequence.

The term "introduction" in which a nucleic acid sequence is inserted into a cell means "transfection", or "transformation" or "transduction", and the reference to the integration of a nucleic acid sequence into an eukaryotic cell or a prokaryotic cell is included, and in this case, the nucleic acid sequence is integrated into a genome (for example, a chromosome, a plasmid, a choromatophore, or mitochondrial DNA) of a cell, and thus is converted into an autonomous replicon, or transiently expressed.

The medicine composition of the present invention metabolizes agar, agarose, neoagarohexaose, or agarotriose into AHG having anti-inflammatory and anti-cancer activities, and thus may be used for preventing or treating cancer or an inflammatory disease.

As used herein, the term "prevention" refers to all actions that suppress or delay the onset of cancer or an inflammatory disease by administering the medicine composition of the present invention to a subject.

As used herein, the term "treatment" refers to all actions that ameliorate or beneficially change symptoms of cancer or an inflammatory disease by administering the medicine composition of the present invention to a subject.

As used herein, 'effective amount' refers to an amount of a compound capable of exhibiting an anti-cancer effect or suppressing inflammation.

The cancer may be colon cancer, cervical cancer, breast cancer, gastric cancer, liver cancer, and the like.

As used herein, 'anti-inflammatory effect' or 'anti-inflammatory activity' refers to the suppression of inflammation, and the inflammation is one of the defense responses of a living tissue to a certain stimulus, and refers to a complicated lesion involving three things: tissue degeneration, circulatory disturbance and exudation, and tissue proliferation. More specifically, inflammation is part of innate immunity, and human innate immunity recognizes cell surface patterns specifically present in pathogens, like in other animals. Phagocytes recognize cells having such surfaces as non-self and attack pathogens. If pathogens break through the physical barriers of the body, an inflammatory response occurs. The inflammatory response is a non-specific defense action that creates a hostile environment for the microorganisms that have invaded a wound site. In the inflammatory response, when a wound occurs or an external infectious agent enters the body, the leukocytes responsible for the immune response in the initial stage cluster and express cytokines. Therefore, the expression level of intracellular cytokines is an index of inflammatory response activation.

The inflammatory disease includes general inflammatory symptoms such as edema, and may include inflammatory bowel disease, peritonitis, osteomyelitis, cellulitis, pancreatitis, traumatic shock, bronchial asthma, allergic rhinitis, cystic fibrosis, acute bronchitis, chronic bronchitis, acute bronchiolitis, chronic bronchiolitis, osteoarthritis, gout, spondyloarthropathy, ankylosing spondylitis, Reiter's syndrome, psoriatic arthropathy, enteropathic spondylitis, juvenile arthropathy, juvenile ankylosing spondylitis, reactive arthropathy, infectious arthritis, post-infectious arthritis, gonococcal arthritis, tuberculous arthritis, viral arthritis, fungal arthritis, syphilitic arthritis, Lyme disease, arthritis associated with 'vasculitis syndrome', polyarteritis nodosa, hypersensitivity vasculitis, Lou Gehrig's granulomatosis, polymyalgia rheumatica, articular cell arteritis, calcium crystal deposition arthropathy, pseudogout, non-joint rheumatism, bursitis, tenosynovitis, epicondylitis (tennis elbow), neuropathic joint disease (or referred to as 'Charcot joint'), hemarthrosis, Henoch-Schönlein purpura, hypertrophic osteoarthropathy, multicentric reticulohistiocytoma, scoliosis, hemochromatosis, hemoglobinopathy, hyperlipoproteinemia, hypogammaglobulinemia, familial Mediterranean fever, Behcet's disease, systemic lupus erythematosus, relapsing fever, multiple sclerosis, sepsis, septic shock, acute respiratory distress syndrome, multiple organ dysfunction syndrome, chronic obstructive pulmonary disease, rheumatoid arthritis, acute lung injury, bronchopulmonary dysplasia, diabetes mellitus type II, arteriosclerosis, dementia of Alzheimer's type, familial cold autoinflammatory syndrome, Muckle-Wells syndrome, neonatal mutisystem inflammatory disease, chronic infantile neurologic cutaneous articular syndrome, adult-onset Still's disease, contact dermatitis, hydatidiform mole, syndrome of pyogenic arthritis, pyoderma gangrenosum, and acne, hyperimmunoglobulin D syndrome, cryopyrin-associated periodic syndrome, and the like.

The medicine composition of the present invention may further include a pharmaceutically acceptable carrier.

The pharmaceutically acceptable carrier includes a carrier and a vehicle typically used in the medical field, and specific examples thereof include an ion exchange resin, alumina, aluminum stearate, lecithin, a serum protein (for example, a human serum albumin), a buffer material (for example, various phosphates, glycine, sorbic acid, potassium sorbate, partial glyceride mixture of saturated vegetable fatty acid), water, a salt or electrolyte (for example, protamine sulfate, dissodium hydrogen phosphate, potassium hydrogen phosphate, sodium chloride, and zinc salts), colloidal silica, magnesium trisilicate, polyvinylpyrrolidone, a cellulose-based substrate, polyethylene glycol, sodium carboxymethylcellulose, polyarylate, wax, polyethylene glycol, wool, or the like, but are not limited thereto.

In addition, the medicine composition of the present invention may additionally include a lubricant, a wetting agent, an emulsifier, a suspending agent, a preservative, or the like, in addition to the aforementioned ingredients.

As an aspect, the medicine composition of the present invention may be formulated and used in various dosage forms suitable for oral or parenteral administration.

Non-limiting examples of the preparations for oral administration include troches, lozenges, tablets, aqueous suspensions, oily suspensions, prepared powders, granules, emulsions, hard capsules, soft capsules, syrups, elixirs, or the like.

To formulate the medicine composition of the present invention for use for oral administration, a binder such as lactose, saccharose, sorbitol, mannitol, starch, amylopectin, cellulose, or gelatin; an excipient such as dicalcium phosphate; a disintegrating agent such as corn starch or sweet potato starch; a lubricant such as magnesium stearate, calcium stearate, sodium stearyl fumarate, or polyethylene glycol wax; or the like may be used, and a sweetener, a fragrance, syrup, or the like may also be used.

Furthermore, in the case of capsules, in addition to the above-mentioned materials, liquid carriers such as fatty oils may be further used.

Non-limiting examples of the preparations for parenteral administration include injections, suppositories, respiratory inhalation powders, aerosols for spray, oral sprays, oral cleansers, toothpastes, ointments, powder for application, oils, creams, and the like.

To formulate the medicine composition of the present invention for use for parenteral administration, sterilized aqueous solutions, non-aqueous solvents, suspensions, emulsions, freeze-dried preparations, agents for external application, or the like may be used, and as the non-aqueous solvents and the suspensions, propylene glycol, polyethylene glycol, a vegetable oil such as olive oil, an injectable ester such as ethyl oleate, or the like may be used.

In addition, more specifically, when the medicine composition of the present invention is formulated as an injection, the medicine composition of the present invention may be mixed in water with a stabilizer or a buffer to be prepared into a solution or a suspension, which is then formulated into a unit dosage form such as an ampoule or a vial. In addition, when the medicine composition of the present invention is formulated as an aerosol, a propellant or the like may be mixed with an additive to disperse a water-dispersed concentrate or wet powder.

In addition, when the medicine composition of the present invention is formulated as an ointment, a cream, or the like, the medicine composition may be formulated using, as a carrier, an animal oil, a vegetable oil, wax, paraffin, starch, tragacanth, cellulose derivatives, polyethylene glycol, silicone, bentonite, silica, talc, zinc oxide, or the like.

A pharmaceutically effective amount and an effective dose of the medicine composition of the present invention may vary depending on the formulation method, administration mode, administration schedule and/or administration route, or the like, and may vary depending on various factors including the type and degree of the reaction to be achieved via administration of the medicine composition of the present invention, the type, age, body weight, and general health status of an individual to which the composition is administrated, the symptoms or severity of diseases, gender, diet, excretion, drugs used simultaneously or at different times in the corresponding individual, ingredients of other compositions, and the like and similar factors well known in the medical field, and the effective dose for desired treatment may be easily determined and prescribed by a person with ordinary skill in the art. The medicine composition of the present invention may be administered once or several times daily. Thus, the dose is not intended to limit the scope of the present invention in any way.

The administration route and administration mode of the medicine composition of the present invention may be independent from each other, the administration method is not particularly limited, and the administration route and the administration mode may follow an arbitrary administration route and administration mode as long as they enable the medicine composition to reach the corresponding site to be targeted. The medicine composition may be administered orally or parenterally.

The parenteral administration may use, for example, intravenous administration, intraperitoneal administration, intramuscular administration, transdermal administration, subcutaneous administration, or the like, a method for applying or spraying the medicine composition on a disease site, or inhaling the medicine composition may also be used, but the methods are not limited thereto.

The medicine composition of the present invention may be preferably administered orally or by injection.

The present invention also provides a method for treating cancer or an inflammatory disease, the method including: administering a therapeutically effective amount of the medicine composition to a subject.

As used herein, the term "subject" refers to all animals including mammals including rats, livestock, humans, and the like.

In a method for treating cancer or an inflammatory disease of the present invention, the description on the dosage, administration route, administration mode, and the like of the medicine composition is the same as that described above in relation to the medicine composition. Further, the type of cancer or inflammatory disease is also the same as that described above in relation to the medicine composition.

The present invention also provides a food composition including: one or more substrates selected from the group consisting of agar, agarose, neoagarohexaose, and agarotriose; a *Bacteroides plebeius* strain; and a *Bifidobacterium* strain.

The food composition may be prepared into a food formulation prepared by encapsulation, pulverization, suspension or the like.

Since the food dosage form can be taken on a daily basis, the food dosage form can be expected to prevent or alleviate cancer or an inflammatory disease, and is very useful.

The type of food is not particularly limited and includes, for example, dairy products, health foods in a typical sense, and the like.

The present invention also provides a method for preparing agarotriose, the method including:
reacting a reaction product with a neoagarobiose hydrolase of SEQ ID NO: 2 or 6, wherein the reaction product is obtained by reacting any one substrate of agar, agarose or neoagarheaose with a β-agarase of SEQ ID NO: 1 or 5; and
purifying agarotriose from the resulting product through a size-exclusion column.

In case of the conventional process (A of FIG. 13), in which an enzymatic hydrolysis is performed after a weak acid pre-treatment, produces large amounts of salts in the neutralization process and when a low-concentration neutral buffer is used, a pre-treatment reaction needs to be performed at a high temperature (170° C.), so that a high-temperature and high pressure reactor is required. In addition, the production yield of agarotriose is considerably low due to the focus on improvement of the production yield of AHG, and particularly, acetic acid used for the pre-treatment causes an unpleasant odor. For such reasons, there may be problems in using agarotriose as a prebiotic material. Therefore, the method for preparing agarotriose of the present invention solves the above-described problems by the following method.

First, a pre-treatment process is omitted by applying a β-agarase which usually produces neoagarotetraose which is a precursor for agarotriose during the production of agarotriose, and high yields of agarotriose, AHG, and D-Gal are obtained through a two-step enzymatic reaction (that is, an endo type β-agarase, a neoagarobiose hydrolase) under mild conditions.

Figure 13:
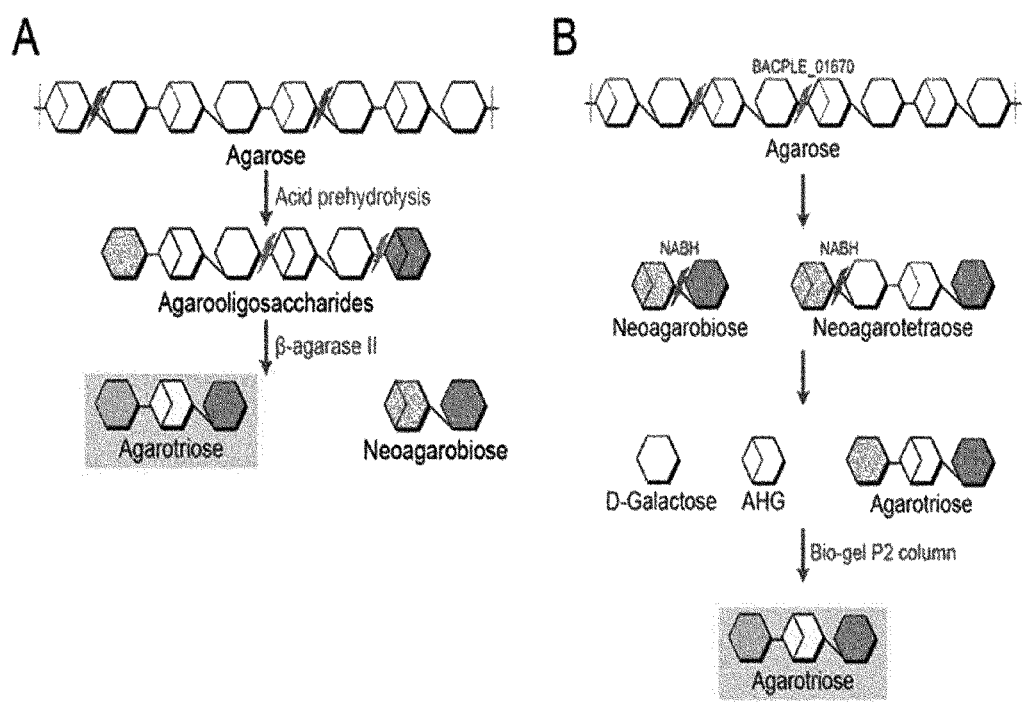
FIG. 13 illustrates a schematic view of a process of producing and isolating agarotriose from agarose (A: process of producing agarotriose through acid treatment and enzymatic saccharification, B: process of producing and purifying AHG, D-Gal, and agarotriose through enzymatic saccharification).

Second, during the purification of agarotriose, monosaccharides and trisaccharides are separated through a size exclusion Bio-P2 gel column using the difference in degree of polymerization, using a size exclusion chromatography technique, thereby obtaining high-purity agarotriose (B of FIG. 13). Since this purification process uses water as a mobile phase without using an organic solvent harmful to the human body and little agarotriose is lost during the purification process, the purification process has an advantage in that purified high-yield agarotriose can be obtained.

The β-agarase degrades any one substrate of agar, agarose, or neoagarohexaose into neoagarobiose and neoagarotetraose which are neoagarooligosaccharides, and a β-agarase of SEQ ID NO: 1 derived from the above-described *Bacteroides plebeius* DSM 17135 strain may be used, or a heat-resistant agarase of SEQ ID NO: 5, which uses agar or agarose as a substrate to degrade the substrate into neoagarotetraose and neoagarohexaose may be used.

The heat-resistant agarase may be derived from *Saccharophagus degradans* $2\text{-}40^T$, but is not particularly limited thereto.

The heat-resistant agarase may be isolated and purified from a supernatant of a *Saccharophagus degradans* $2\text{-}40^T$ culture product, and may be produced and isolated from strains other than *Saccharophagus degradans* $2\text{-}40^T$ using a genetic engineering recombinant technology, an artificial chemical synthesis method, or the like. When the genetic engineering recombinant technology is used, it may be replaced by a supernatant or supernate fluid of a culture product of a transformed *E. coli*, but the technology is not particularly limited thereto.

The reaction of any one substrate of agar, agarose, or neoagarohexaose and the β-agarase may be performed at 0 to 200 rpm under a temperature condition of 30 to 60° C. for 5 minutes to 12 hours.

The neoagarobiose hydrolase degrades neoagarobiose and neoagarotetraose into AHG, D-Gal, and agarotriose, and a neoagarobiose hydrolase of SEQ ID NO: 2 derived from the above-described *Bacteroides plebeius* DSM 17135 may be used or an alpha-neoagarobiose hydrolase of SEQ ID NO: 6 derived from *Saccharophagus degradans* $2\text{-}40^T$ may be used.

The *Saccharophagus degradans* $2\text{-}40^T$-derived alpha-neoagarobiose hydrolase may be isolated and purified from a supernatant or supernate fluid of a culture product of *Saccharophagus degradans* $2\text{-}40^T$, and may be produced and purified from strains other than *Saccharophagus degradans* $2\text{-}40^T$ using a genetic engineering recombinant technology, an artificial chemical synthesis method, or the like.

A reaction of a reaction product of the β-agarase and the neoagarobiose hydrolase may be performed at 0 to 200 rpm under a temperature condition of 25 to 45° C. for 30 minutes to 12 hours.

After monosaccharides AHG and D-Gal and a trisaccharide agarotriose produced by the neoagarobiose hydrolase are obtained, purified agarotriose with high purity and high yield may be obtained using a size exclusion column.

Hereinafter, the present invention will be described in more detail through the Examples according to the present invention, but the scope of the present invention is not limited by the Examples suggested below.

Example 1

Experiment of Degrading Agarose by β-Agarase

An enzymatic reaction was performed in order to produce agar-derived oligosaccharides at various degrees of polymerization, including agarotriose from agarose which is a main carbohydrate constituting red algae. First, an enzymatic reaction of Aga16B, which is a *S. degradans* $2\text{-}40^T$-derived endo-type agarase, was performed using a 1% (w/v) concentration of agarose as a substrate. In this case, the enzymatic reaction of Aga16B was performed at 50° C. and 200 rpm for 2 hours.

Figure 2:
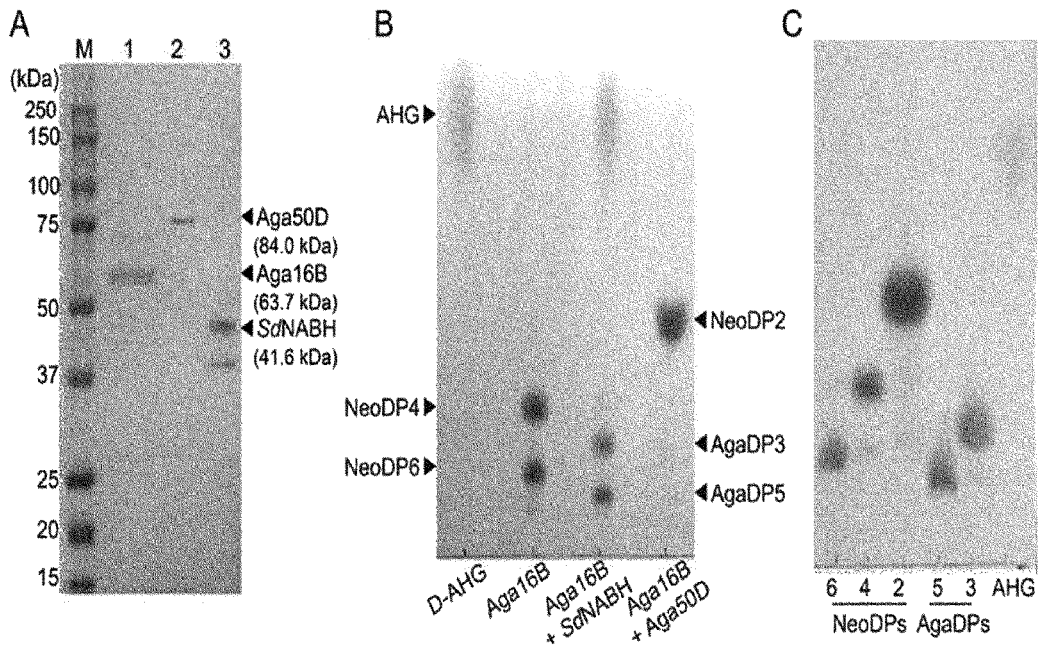
FIG. 2 illustrates the results (A) of purifying recombinant proteins of a *Saccharophagus degradans* (*S. degradans*) 2-40$^T$-derived endo type β-agarase Aga16B, an exo type β-agarase Aga50D, and an alpha-neoagarobiose hydrolase SdNABH, the results (B) of producing oligosaccharides with various degrees of polymerization, neoagarobiose, and AHG from agarose through an enzymatic reaction, and results (C) of purifying sugars through size-exclusion chromatography of enzyme reaction products of agarose with a *Bacteroides plebeius* DSM 17135-derived endo type β-agarase enzyme BpGH16A (BACPLE_01670) and a neoagarobiose hydrolase BpGH117 (BACPLE_01671).

As a result of the enzymatic reaction, neoagarotetraose (NeoDP4) and neoagarohexaose (NeoDP6) were produced (B of FIG. 2).

Agarotriose (DP3), agaropentaose (DP5), and AHG were produced through an enzymatic reaction of a a next-step enzyme, *S. degradans* $2\text{-}40^T$-derived neoagarobiose hydrolase (SdNABH) and the reaction products as substrates. The SdNABH enzymatic reaction was performed at 30° C. and 200 rpm for 2 hours.

Further, a disaccharide body neoagarobiose (NeoDP2) was produced through an enzymatic reaction of Aga50D, a *S. degradans* $2\text{-}40^T$-derived exo-type agarase and the Aga16B reaction products as substrates. The Aga50D enzymatic reaction was performed at 30° C. and 200 rpm for 2 hours.

Next, the enzymatic reaction conditions of BpGH16A (BACPLE_01670) which is an endo type β-agarase derived from an intestinal microorganism *Bacteroides plebeius* DSM 17135 were as follows: enzyme loading amount: 8 mg of BpGH16A/g agarose, buffer: 20 mM Tris-HCl (pH 7.0), and reaction temperature and time: 40° C. and 2 hours.

The enzymatic reaction conditions of a neoagarobiose hydrolase BpGH117 (BACPLE_01671) were as follows: enzyme loading amount: 4 mg of BpGH117/g neoagarobiose, buffer: 20 mM Tris-HCl (pH 7.0), and reaction temperature and time: 40° C. and 2 hours.

As illustrated in C of FIG. 2, agarotriose and AHG may be produced from agarose through a reaction combination of agar degradation-associated enzymes derived from an intestinal microorganism *Bacteroides plebeius* DSM 17135. As a result of analyzing the reaction products by thin layer chromatography (TLC), neoagarotetraose (NeoDP4) was produced as a main product (Lane 2) from an agarose substrate (Lane 1) through a BpGH16A (BACPLE_01670) enzymatic reaction. Thereafter, agarotriose and AHG were produced (Lane 2) through a BpGH117 (BACPLE_01671) enzymatic reaction. Even when the two enzymes were simultaneously reacted, agarotriose and AHG were mainly produced (Lane 3) in the same manner as when the two enzymes were sequentially reacted.

Example 2

Recombination and Enzymatic Reaction Experiment of *Bacteroides Plebeius* DSM 17135-Derived Endo Type β-Agarase Enzymes BpGH16A (BACPLE_01670) and BpGH50 (BACPLE_01683) and Neoagarobiose Hydrolase BpGH117 (BACPLE_01671)

Figure 3:
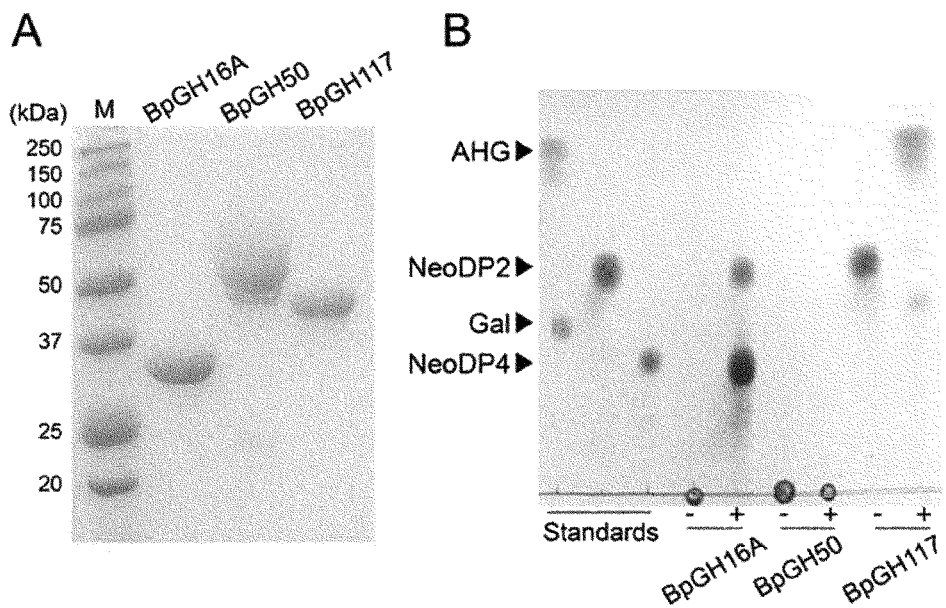
FIG. 3 illustrates the results (A) of purifying each recombinant enzyme of intestinal microorganism *Bacteroides plebeius* DSM 17135-derived endo type β-agarase enzymes BpGH16A (BACPLE_01670) and BpGH50 (BACPLE_01683) and neoagarobiose hydrolase BpGH117 (BACPLE_01671) after being expressed in *E. coli* and results (B) of performing enzymatic reaction experiments.

As illustrated in FIG. 3, in the case of a *Bacteroides plebeius* DSM 17135-derived GH50 family enzyme BpGH50 (BACPLE_01683), β-agarase activity was not exhibited.

Example 3

Experiment of Producing Agarotriose and AHG from Agarose Substrate through Enzymatic Reaction of *Bacteroides Plebeius* DSM 17135-Derived Endo Type β-Agarase Enzyme BpGH16A (BACPLE_01670) and Neoagarobiose Hydrolase BpGH117(BACPLE_01671)

Oligosaccharides at various degrees of polymerization, neoagarobiose, and AHG produced through a reaction of the respective purified recombinant enzymes Aga16B, Aga50D, and SdNABH were purified by size exclusion column chromatography. In this case, Sephadex G-10 was used as a column resin for size-exclusion column chromatography.

Figure 4:
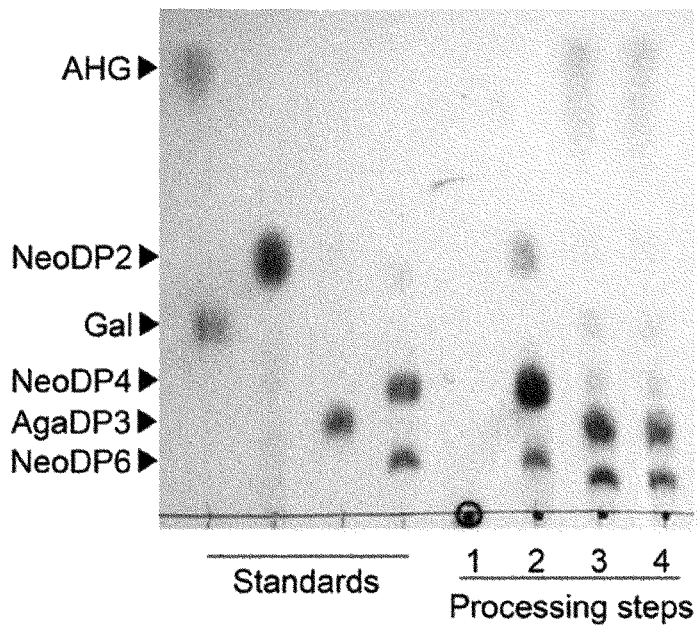
FIG. 4 illustrates the results of producing agarotriose and AHG through an enzymatic reaction of a *Bacteroides plebeius* DSM 17135-derived endo type β-agarase enzyme BpGH16A (BACPLE_01670) and a neoagarobiose hydrolase BpGH117 (BACPLE_01671) from an agarose substrate.

As illustrated in FIG. 4, agarotriose and AHG were produced from agarose through a reaction of an endo type β-agarase enzyme BpGH16A (BACPLE_01670) and a neoagarobiose hydrolase BpGH117(BACPLE_01671).

Example 4

Experiment of Culturing Probiotic Microorganism *Bifidobacterium Longum* subsp. Infantis ATCC 15697 Strain by Adopting Respective Purified Sugars as Carbon Sources using Bioscreen C In order to prove the prebiotic effects of agar-derived sugars, the cell growth of a *Bifidobacterium longum* subsp. *infantis* ATCC 15697 strain which is a *Bifidobacterium* was monitored using each purified sugar, including agarotriose, as a single carbon source. In this case, as a culture composition, 10 g/L of BactoPeptone, 5 g/L of a yeast extract, 2 g/L of $K_2HPO_4$ anhydride, 5 g/L of Na acetate anhydride, 2 g/L of $NH_4$ citrate tribasic, 0.2 g/L of Mg sulfate heptahydrate, 0.05 g/L of Mn sulfate, 1 mL/L of Tween 80 (polysorbate 80), 0.5 g/L of cysteine, and 5 g/L of each purified sugar were used and cultured at 37° C.

Figure 5:
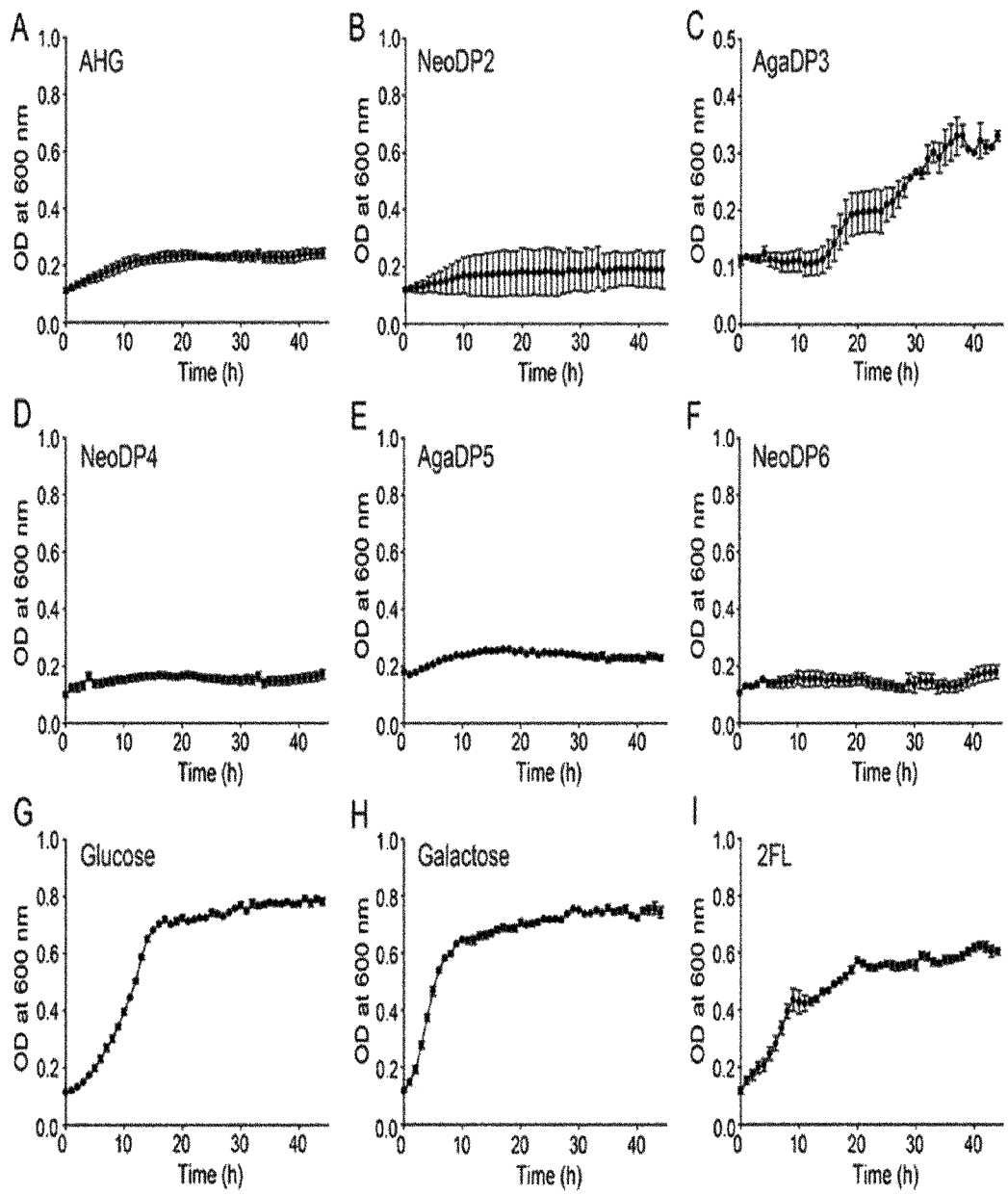
FIG. 5 illustrates the results of culturing a *Bifidobacterium longum* subsp. *infantis* ATCC 15697 strain which is a probiotic microorganism with respective purified sugars as carbon sources, using Bioscreen C (A: AHG, B: NeoDP2, C: AgaDP3, D: NeoDP4, E: AgaDP5, F: NeoDP6, G: Glucose, H: Galactose, I: 2FL).

As illustrated in FIG. 5, it was confirmed that the *Bifidobacterium longum* subsp. *infantis* ATCC 15697 strain selectively fermented only agarotriose among various purified sugars.

Example 5

Analysis of Agarotriose Fermentation Profile of *Bifidobacterium Longum* subsp. *Infantis* ATCC 15697 Strain In order to monitor fermentation products, a *Bifidobacterium longum* subsp. *Infantis* ATCC 15697 strain was cultured under a test tube condition.

Figure 6:
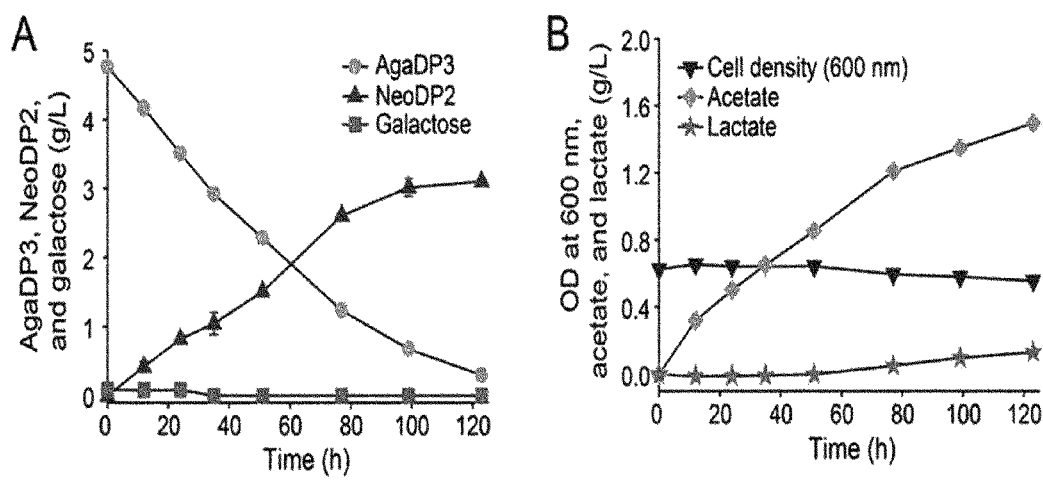
FIG. 6 illustrates the results of analyzing agarotriose fermentation profiles of a *Bifidobacterium longum* subsp. *infantis* ATCC 15697 strain (A: results using AgaDP3, NeoDP2, and galactose as a substrate, B: cell density and acetate and lactate as a substrate).

As illustrated in FIG. 6, the *Bifidobacterium longum* subsp. *infantis* ATCC 15697 degraded agarotriose into galactose and neoagarobiose under a carbon source at a concentration of 5 g/L agarotriose, and galactose was fermented in cells to produce acetic acid. The neoagarobiose was secreted and accumulated outside the cells without being degraded in the cells any more.

Example 6

Degradation Experiments of Agarotriose and Neoagarobiose using Crude Enzyme Solution of *Bifidobacterium Longum* subsp. *Infantis* ATCC 15697 Strain In order to confirm the metabolic pathway of agarotriose, an experiment was performed on a crude enzyme solution of a *Bifidobacterium longum* subsp. *infantis* ATCC 15697 strain. For this purpose, cells and the medium were separated by centrifugation (14,000 rpm, 5 minutes, 4° C.) of a culture solution of *Bifidobacterium longum* subsp. *infantis* ATCC 15697 cultured under an agarotriose condition. An extracellular crude enzyme was obtained by ammonium sulfate precipitation of a supernatant. Further, for a cell-free extract including an intracellular crude enzyme, a supernatant crude enzyme was obtained by re-suspending cells in a 20 mM Tris-HCl buffer, and then lysing the cells by sonication, and centrifuging the lysate. During the crude enzyme experiment, 2 mg/mL of the crude enzyme and 2 mg/mL of agarotriose as a substrate were used to perform a reaction under an enzymatic reaction condition of 30° C. and 200 rpm in a 20 mM Tris-HCl buffer (pH 7.0) for 2 hours.

Figure 7:
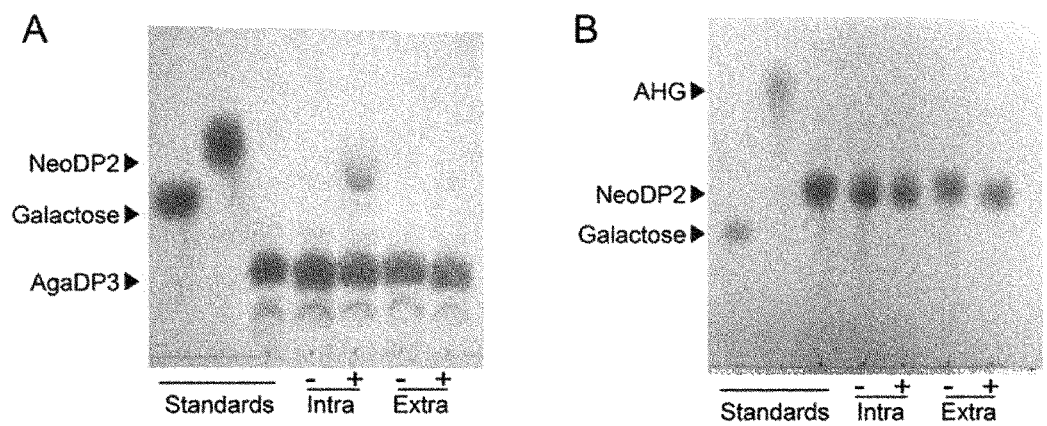
FIG. 7 illustrates the degradation experimental results of agarotriose (A) and neoagarobiose (B) using a crude enzyme solution of a *Bifidobacterium longum* subsp. *infantis* ATCC 15697 strain.

As illustrated in FIG. 7, it was confirmed that a β-galactosidase reaction of degrading agarotriose into galactose and neoagarobiose occurred in the cell-free extract including an intracellular crude enzyme. In addition, it was confirmed that the activity of the crude enzyme against neoagarobiose was not exhibited.

Example 7

Recombinant Protein Production and Enzymatic Reaction Experiments of Four β-Galactosidase-Encoding Genes (Blon_2016, Blon_2123, Blon_2334, and Blon_2416) of a *Bifidobacterium Longum* subsp. *Infantis* ATCC 15697 Strain In order to confirm which enzyme gene had the activity of degrading agarotriose, after all of the four β-galactosidases of the *Bifidobacterium longum* subsp. *infantis* ATCC 15697 were cloned, the enzymatic activity was tested by overexpressing the four β-galactosidases in *E. coli* and purifying each enzyme protein.

Figure 8:
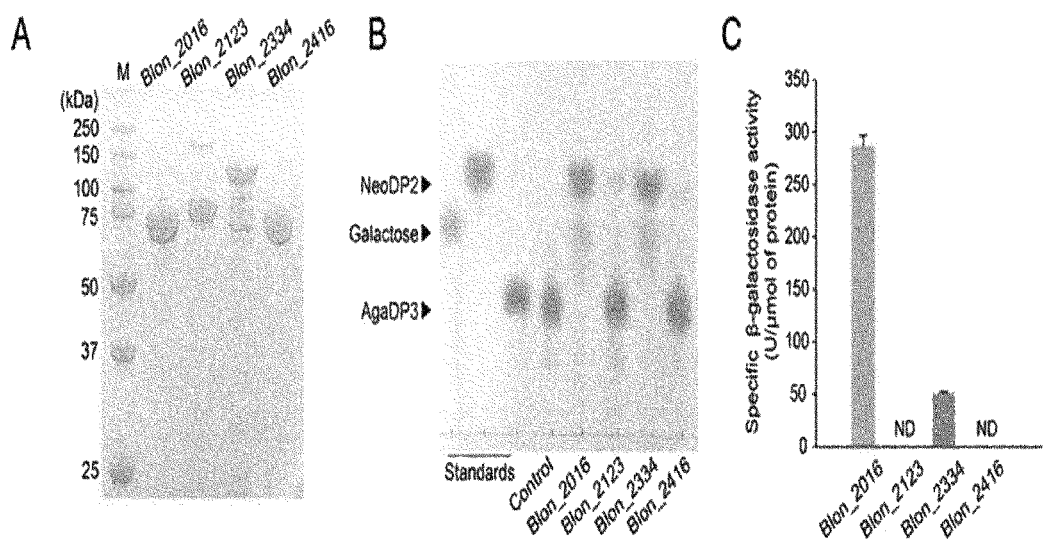
FIG. 8 illustrates the results of performing an enzymatic reaction after cloning four β-galactosidase-encoding genes (Blon_2016, Blon_2123, Blon_2334, and Blon_2416) of a *Bifidobacterium longum* subsp. *infantis* ATCC 15697 strain and producing and purifying recombinant proteins from *E. coli* (A: Gel photograph, B: TLC results, C: β-galactosidase specific activity of respective enzymes for an agarotriose substrate).

As illustrated in FIG. 8, it was confirmed that proteins of two enzyme genes Blon_2016 and Blon_2334 exhibited activity.

Example 8

Experiment of the Fermentation Ability of Agarotriose by other Strains belonging to *Bifidobacterium Longum* subsp. *Infantis*

In order to confirm whether agarotriose also had prebiotic effects on probiotic microorganisms other than a *Bifidobacterium longum* subsp. *infantis* ATCC 15697 strain, Bifidobacterium longum subsp. *infantis* ATCC 17930, *Bifidobacterium longum* subsp. *infantis* ATCC 15702, *B. bifidum* DSM 20082, and *B. kashiwanohense* DSM 21854 were cultured under agarotriose single carbon source conditions.

Figure 9:
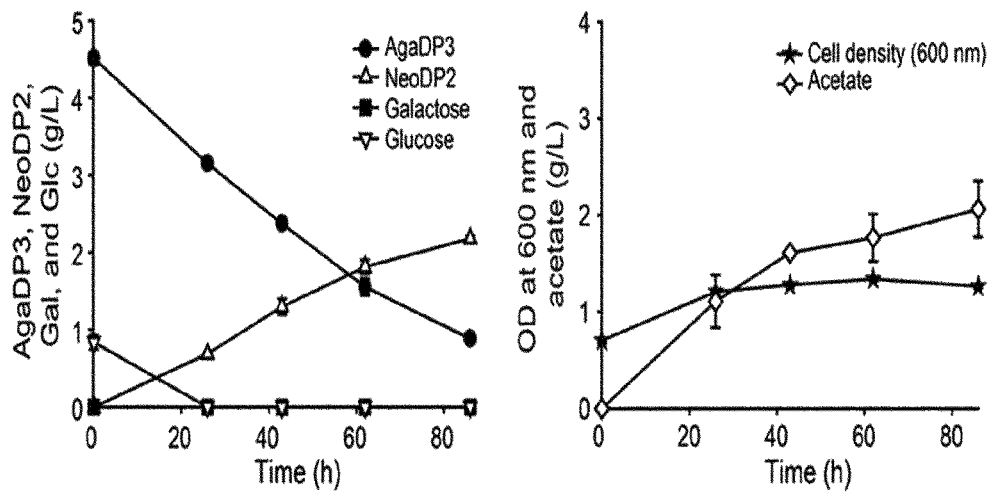
FIG. 9 illustrates the experimental results of the fermentation ability of agarotriose by *Bifidobacterium longum* subsp. *infantis* ATCC 17930 and *Bifidobacterium longum* subsp. *infantis* ATCC 15702 strains which are other strains belonging to *Bifidobacterium longum* subsp. *Infantis* (A: *Bifidobacterium longum* subsp. *Infantis* ATCC 17930, B: *Bifidobacterium longum* subsp. *infantis* ATCC 15702).
Figure 9:
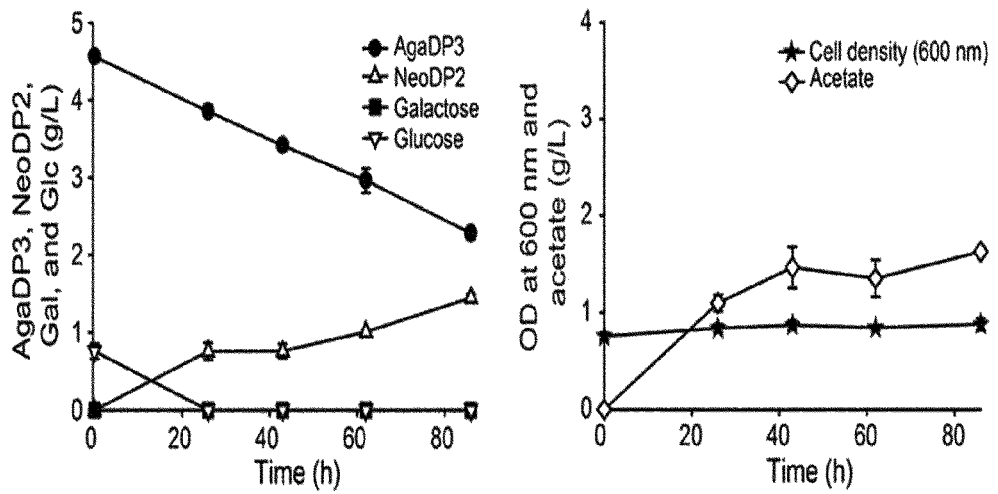
Figure 10:
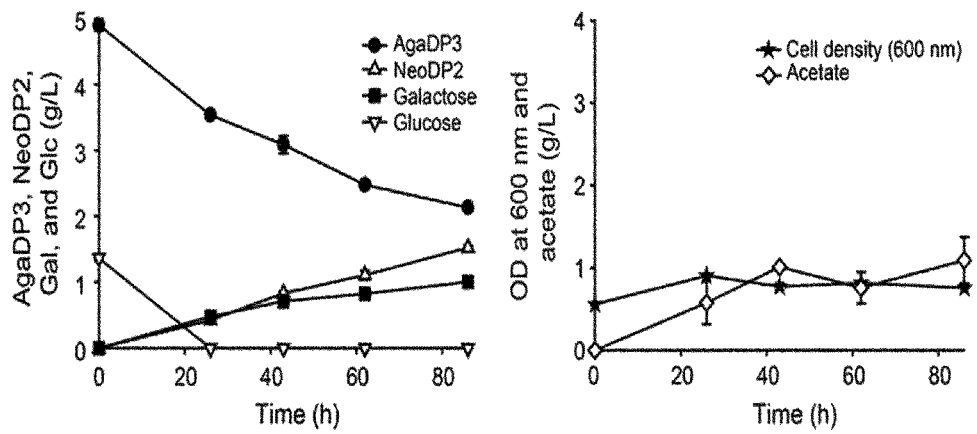
FIG. 10 illustrates the experimental results of the fermentation ability of agarotriose by *B. bifidum* DSM 20082 and *B. kashiwanohense* DSM 21854 strains to ferment agarotriose (A: *B. bifidum* DSM 20082, B: *B. kashiwanohense* DSM 21854).
Figure 10:
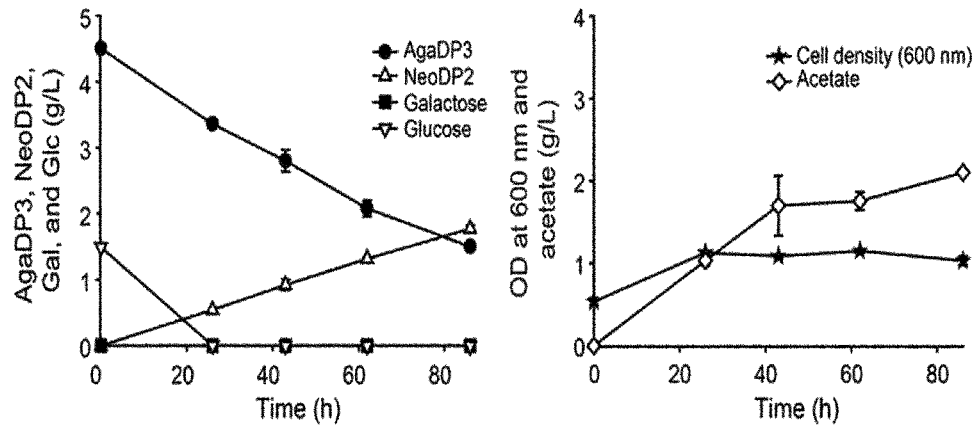

As illustrated in FIGS. 9 and 10, all four probiotic microorganisms metabolized agarotriose and degraded agarotriose into galactose and neoagarobiose in the same manner as in *Bifidobacterium longum* subsp. *infantis* ATCC 15697, and then acetic acid was produced by fermenting galactose.

Example 9

Stability Test of Agarotriose against Artificial Gastric Juice

In order to test whether agarotriose could reach the intestines without being degraded, agarotriose was reacted in artificial gastric juice for each time, and then it was confirmed whether agarotriose was degraded, using TLC and HPLC.

Figure 11:
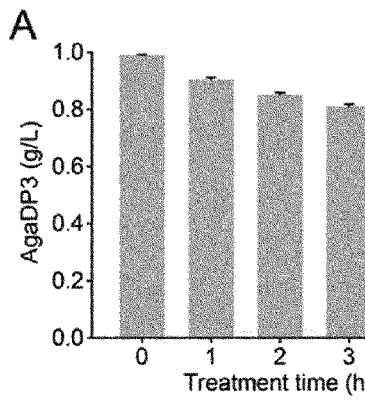
FIG. 11 illustrates the stability test results of agarotriose against artificial gastric juice (A: illustrates TLC results as a graph, B: HPLC results).
Figure 11:
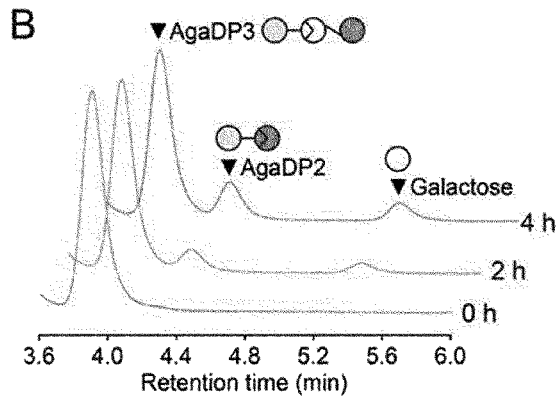

As illustrated in FIG. 11, it was confirmed that after being reacted at 37° C. for 3 hours, 80% or more of agarotriose remained.

Figure 12:
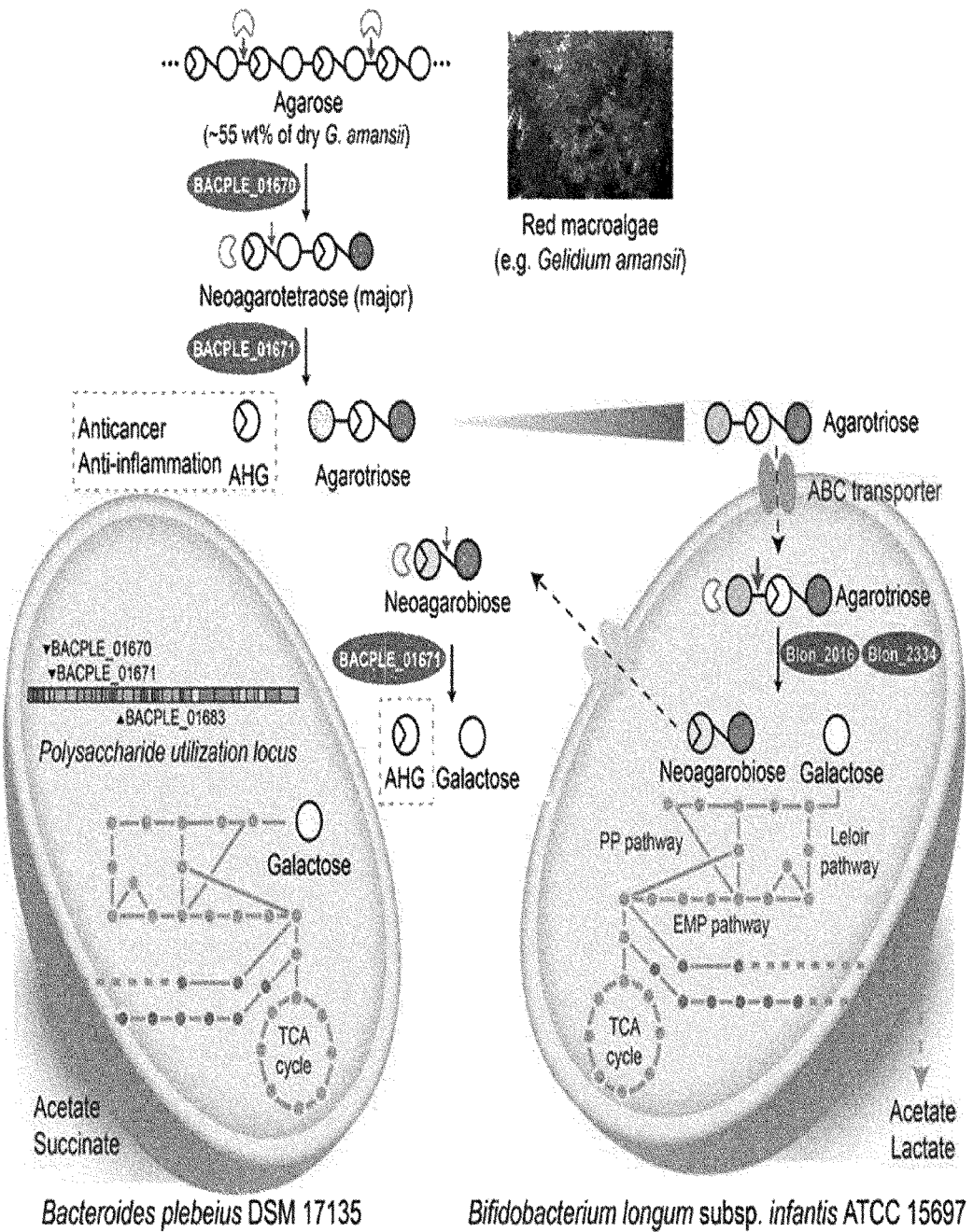
FIG. 12 illustrates the metabolic pathway of agarose by intestinal microorganisms *Bacteroides plebeius* DSM 17135 and *Bifidobacterium longum* subsp. *infantis* ATCC 15697.

From the result, it was firstly confirmed that agarotriose is a novel red algae-derived prebiotic, and a material that is selectively fermented by probiotics. Agarotriose may be produced by enzymatic actions of agarases and NABH from marine derived-*S. degradans* 2-40$^T$ or intestinal microorganism-derived *Bacteroides plebeius* (FIG. 12). Agarotriose is transported into cells by the ABC transporter-related gene of the probiotic *Bifidobacter*, and is degraded into galactose and neoagarobiose by intracellular β-galactosides, and galactose is used for acetic acid fermentation. In addition, neoagarobiose may be degraded into galactose and AHG in the intestines by a neoagarobiose hydrolase from an intestinal microorganism *Bacteroides plebeius*. Since AHG is known as a bioactive material having a colon cancer prevention effect and anti-inflammatory functionality, agarotriose may exhibit not only prebiotic activity, but also colon cancer prevention and anti-inflammatory bioactivities due to AHG produced through the metabolism by intestinal microorganisms *Bifidobacter* and *Bacteroides plebeius* (FIG. 12).

Example 10

Production of BACPLE_01670 and NABH Recombinant Enzymes

A *Bacteroides plebeius*-derived β-agarase hydrolase BACPLE_01670 gene was introduced into *E. coli* BL21 (DE3) using a pET21a vector. In order to pre-culture the recombinant *E. coli* introduced the gene, the recombinant *E. coli* was cultured at 37° C. for 9 hours in a 10 mL LB broth containing 100 μg/mL of ampicillin in a 50-mL-conical tube. Thereafter, after 10 ml of the pre-culture solution was inoculated into 1 L of the main culture solution having the same medium composition, 0.1 mM isopropyl-β-D-thiogalactopyranoside (IPTG) was added thereto when the optical density value showed growth to a mid-exponential step (OD 0.4 to 0.6), and an intracellular protein was expressed by induction at 16° C. for 16 hours. Thereafter, the cell culture solution was transferred to a 500 mL-tube and centrifuged at 10,000 rpm at 4° C. for 30 minutes, and then cells were obtained. In order to prevent protein denaturation, cells collected in 30 mL of a Tris buffer (20 mM Tris-HCl, pH 7.0) were freed again, and the cells were lysed using a sonicator. Thereafter, the cells were centrifuged at 16,000 rpm at 4° C. for 1 hour. The proteins were purified using a HisTrap column (5 ml GE Healthcare), and then the size of each purified protein was confirmed using an SDS-PAGE gel. The salt (imidazole) used for protein purification was removed using a desalting column. The concentration of the recombinant protein from which the salt was removed was quantified by a BCA analysis method.

Next, a *Saccharophagus degradans* 2-40$^T$-derived alpha-neoagarobiose hydrolase NABH gene was introduced into *E. coli* BL21 (DE3) using a pET21a vector, and the recombinant protein was prepared as described above.

Example 11

Enzymatic Reaction of BACPLE_01670 and NABH

During the BACPLE_01670 enzymatic reaction, a 1% (w/v) concentration agarose was used as a substrate, and a reaction was performed under conditions of 50° C. and 100 rpm for 10 hours in a 20 mM Tris-HCl buffer (pH 7.0).

An NABH enzymatic reaction was performed using BACPLE_01670 enzymatic reaction products neoagarotetraose and neoagarobiose as substrates, and an enzymatic reaction was performed under conditions of 37° C. and 100 rpm for 10 hours.

The reaction products after the enzymatic reaction in each step were analyzed by TLC. For the TLC analysis conditions, 1 μl of enzymatic reaction products were loaded onto a silica gel plate as a stationary phase, n-butanol: ethanol: water at 3:1:1 (v/v/v) as a mobile phase solvent was eluted for 1 hour, and then colors were developed using 10% sulfuric acid in ethanol and 0.2% 1,3-dihydroxynaphthalene in ethanol.

Figure 14:
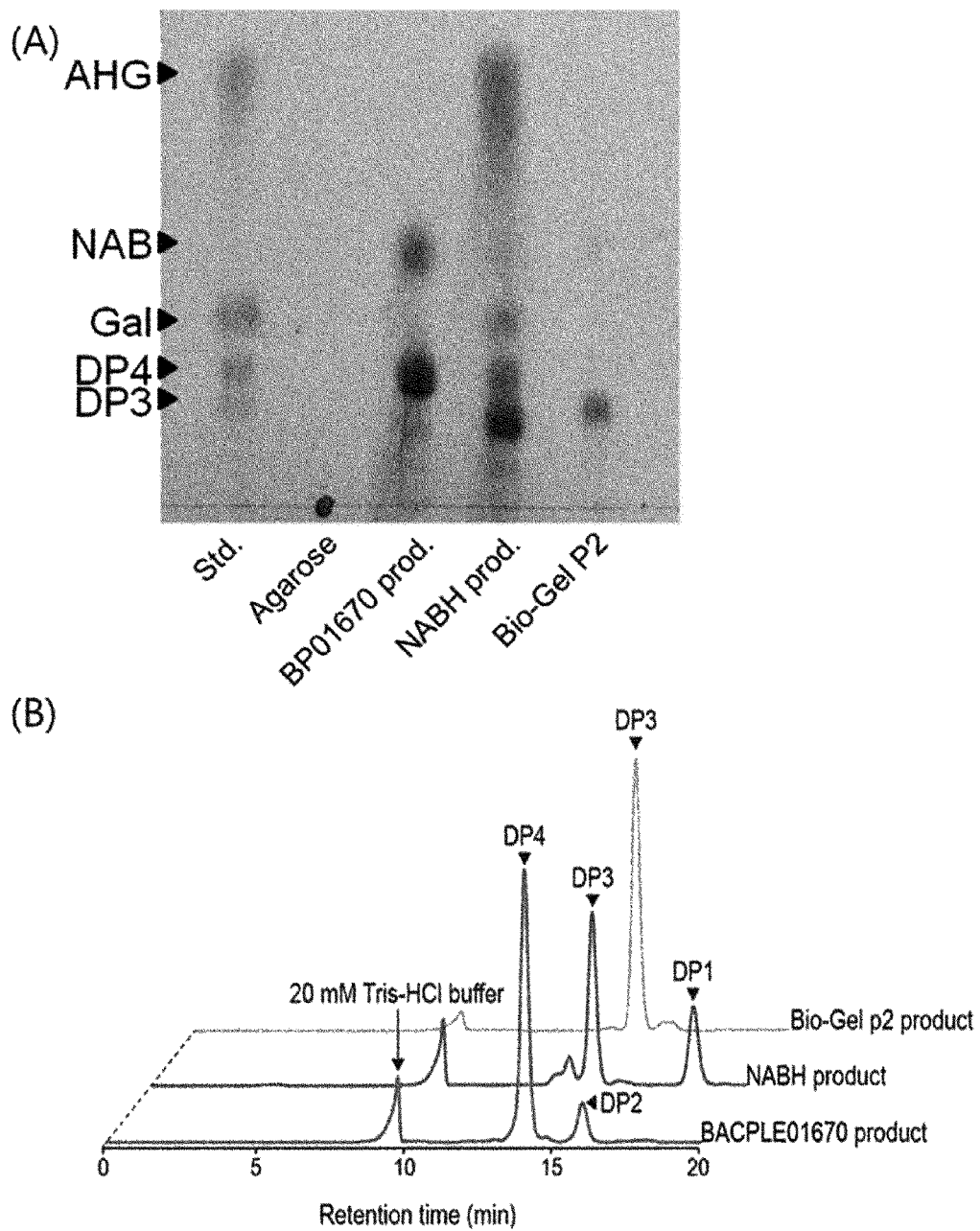
FIG. 14 illustrates the production of agarotriose from agarose through a two-step enzymatic reaction and the results of purifying agarotriose using a size-exclusion column (A: TLC results, B: HPLC results).

As illustrated in A of FIG. 14, agarose was degraded into neoagarooligosaccharides through an enzymatic reaction of an endo type β-agarase BACPLE_01670, and in this case, the main products were neoagarobiose and neoagarotetraose corresponding to DP2 and DP4 as a degree of polymerization (DP). Thereafter, through an enzymatic reaction of an alpha-agarase neoagarobiose hydrolase (NABH), trisaccharides agarotriose and AHG were produced from DP4, and D-galactose and AHG were produced from DP2.

Example 12

HPLC Analysis of BACPLE_01670 Enzymatic Reaction Products

Materials produced during the BACPLE_01670 enzymatic reaction were neoagarotetraose (DP4) and neoagarobiose (DP2) (B of FIG. 14). Among them, a precursor for making agarotriose is neoagarotetraose, and the more the DP4 product, the more agarotriose may be obtained. In order to determine the production ratio of DP4 from BACPLE_01670, the production ratio was calculated using an HPLC KS-802 size exclusion column.

Figure 15:
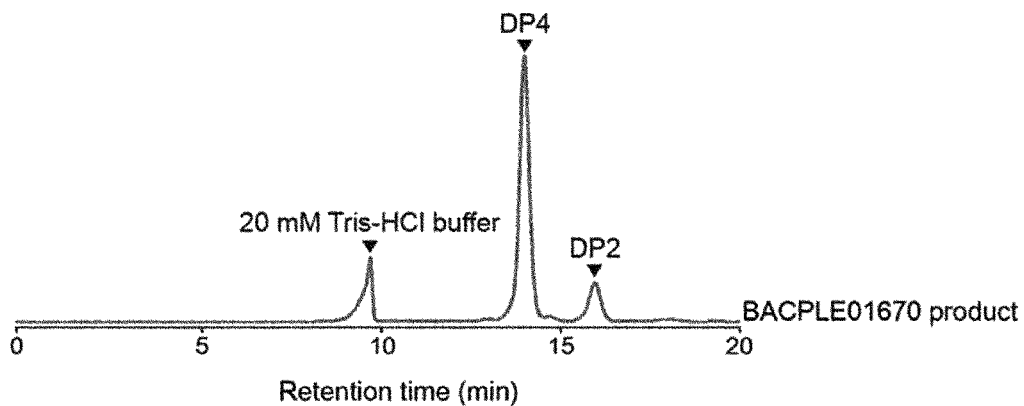
FIG. 15 is an HPLC quantitative analysis result showing the ratio of neoagarotetraose and neoagarobiose that are produced from agarose through an enzymatic reaction of a *Bacteroides plebeius* DSM 17135-derived endo type β-agarase enzyme BpGH16A (BACPLE_01670).

As illustrated in FIG. 15, regarding the reaction products of BACPLE_01670, a result of 0.795 g of neoagarotetraose (0.795 g neoagarotetraose/g agarose) and 0.205 g of neoagarobiose (0.205 g neoagarobiose/g agarose) from 1 g of agarose was obtained.

Example 13

Separation of DP3 (Agarotriose) and DP1 (AHG, D-Gal) Using Size-Exclusion Column (Bio Gel-P2 Column)

The final reaction products obtained from Examples 10 and 11 were AHG and D-Gal, and agarotriose, and a sugar separation column was used to separate AHG and D-Gal thereamong from agarotriose. The machine AKTAprime (GE Healthcare) was used. For a mobile phase used to separate the sugars, a column was stabilized for 10 minutes by flowing tertiary distilled water at a flow rate of 0.3 mL/min, and then 1 ml of a solution flowing through the column after injecting 2 mL of the reaction product was transferred per 2 mL-Eppendorf tube, and analyzed through TLC. The TLC analysis conditions were the same as those in Example 11.

Figure 16:
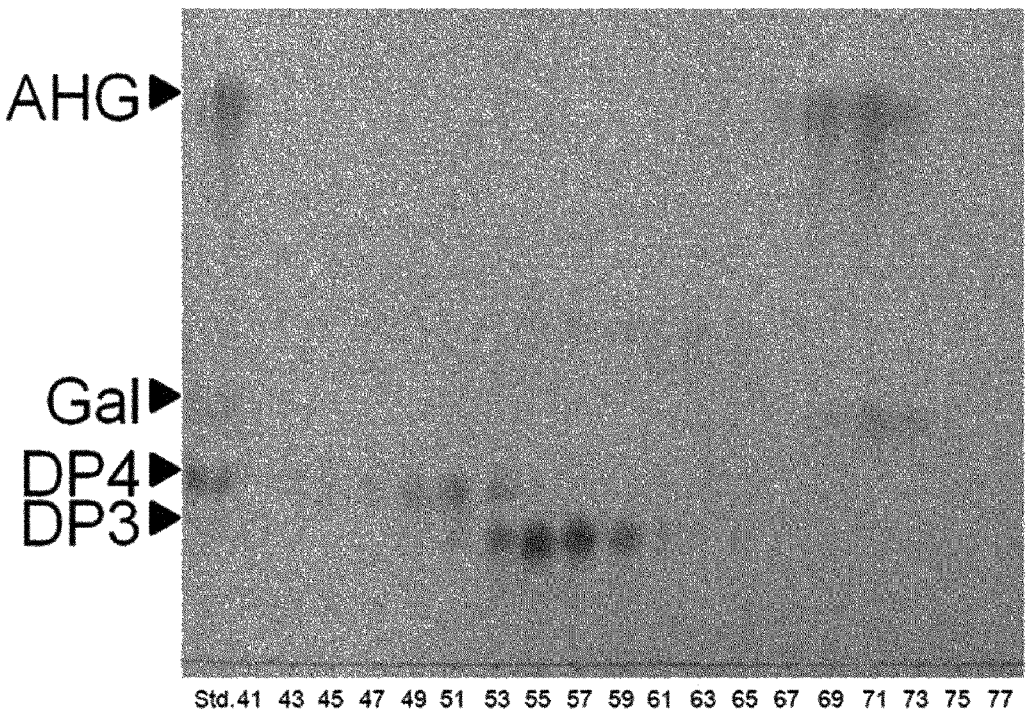
FIG. 16 illustrates the TLC results of analyzing the difference in degree of isolation for each fraction using a size-exclusion column.

As illustrated in FIG. 16, it could be confirmed that as a result of analyzing samples collected by fraction by TLC, DP3 (agarotriose) and DP1 (AHG, D-Gal) were separated.

Example 14

HPLC Quantitative Analysis of Yield and Purity of Agarotriose from Agarose by Enzymatic Saccharification and Separated by Size Exclusion Column After the agarotriose obtained by the sugar separation column in Example 13 was confirmed by TLC, the fraction of agarotriose with high purity was collected. Fractions Nos. 55 to 61 were collected in 15 mL-conical tubes and stirred and well mixed. Thereafter, yield and purity were analyzed through an HPLC KS-802 column by sampling a part of 7 mL.

Figure 17:
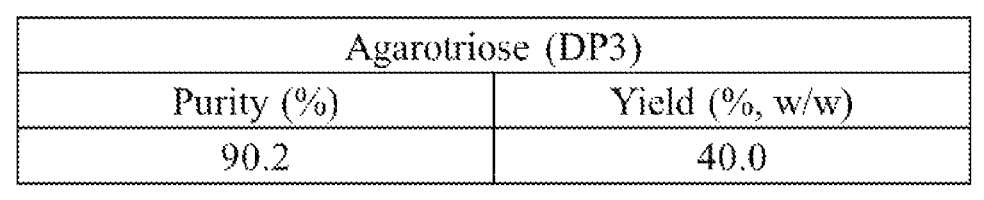

As illustrated in FIG. 17, it was confirmed that 0.4 g of agarotriose was obtained from 1 g of agarose (0.4 g NAB/g agarose), and about 90.2% of the sample was agarotriose.

The present invention can be used as an anti-cancer or anti-inflammatory agent in the fields of food and medicine based on prebiotic characteristics of agarotriose.

---

What is claimed is:

1. A method for producing agarotriose, the method comprising:
   (a) reacting any one substrate of agar, agarose or neoagarohexose with a β-agarase of SEQ ID NO:1 or SEQ ID NO:5;
   (b) reacting the reaction product of step (a) with a neoagarobiose hydrolase of SEQ ID NO: 2 or SEQ ID NO:6, to make a resulting product comprising agarotriose; and
   (c) purifying the agarotriose from the resulting product through a size-exclusion column.

2. The method of claim 1, wherein the β-agarase of SEQ ID NO:1 is an enzyme that is derived from a *Bacteroides plebeius* DSM 17135 strain, and that uses agar, agarose, or neoagarohexaose as a substrate to degrade the substrate into neoagarotetraose and neoagarobiose.

3. The method of claim 1, wherein step (a) is performed at 0 to 200 rpm under a temperature condition of 30 to 60° C. for 5 minutes to 12 hours.

4. The method of claim 1, wherein the neoagarobiose hydrolase of SEQ ID NO:2 is an enzyme that is derived from a *Bacteroides plebeius* DSM 17135 strain, and that uses neoagarotetraose or neoagarobiose as a substrate to degrade the substrate into agarotriose, galactose, or 3,6-anhydro-L-galactose.

5. The method of claim 1, wherein step (b) is performed at 0 to 200 rpm under a temperature condition of 25 to 45° C. for 30 minutes to 12 hours.

* * * * *